(12) United States Patent
Jeynes et al.

(10) Patent No.: US 9,447,080 B2
(45) Date of Patent: *Sep. 20, 2016

(54) VIRAL POLYMERASE INHIBITORS

(71) Applicant: BIOTA SCIENTIFIC MANAGEMENT PTY LTD, Notting Hill (AU)

(72) Inventors: Tyrone Pieter Jeynes, Notting Hill (AU); Alistair George Draffan, Notting Hill (AU); Michael Harding, Notting Hill (AU); Silas Bond, Notting Hill (AU); Rosliana Halim, Notting Hill (AU)

(73) Assignee: BIOTA SCIENTIFIC MANAGEMENT PTY LTD., Victoria (AU)

( * ) Notice: Subject to any disclaimer, the term of this patent is extended or adjusted under 35 U.S.C. 154(b) by 5 days.

This patent is subject to a terminal disclaimer.

(21) Appl. No.: 14/391,500

(22) PCT Filed: Apr. 11, 2013

(86) PCT No.: PCT/AU2013/000369
§ 371 (c)(1),
(2) Date: Oct. 9, 2014

(87) PCT Pub. No.: WO2013/152391
PCT Pub. Date: Oct. 17, 2013

(65) Prior Publication Data
US 2015/0065445 A1   Mar. 5, 2015

Related U.S. Application Data

(60) Provisional application No. 61/623,021, filed on Apr. 11, 2012, provisional application No. 61/623,013, filed on Apr. 11, 2012.

(51) Int. Cl.
| | |
|---|---|
| *A01N 43/00* | (2006.01) |
| *A61K 31/00* | (2006.01) |
| *C07D 405/12* | (2006.01) |
| *A61K 31/427* | (2006.01) |
| *A61K 31/4439* | (2006.01) |
| *A61K 31/706* | (2006.01) |
| *A61K 38/05* | (2006.01) |
| *A61K 38/08* | (2006.01) |
| *A61K 45/06* | (2006.01) |
| *C07D 401/04* | (2006.01) |
| *C07D 401/14* | (2006.01) |
| *C07D 405/14* | (2006.01) |
| *C07D 417/04* | (2006.01) |
| *A61K 31/416* | (2006.01) |
| *C07D 231/56* | (2006.01) |
| *C07D 403/12* | (2006.01) |
| *A61K 38/06* | (2006.01) |

(52) U.S. Cl.
CPC ........... *C07D 405/12* (2013.01); *A61K 31/416* (2013.01); *A61K 31/427* (2013.01); *A61K 31/4439* (2013.01); *A61K 31/706* (2013.01); *A61K 38/05* (2013.01); *A61K 38/06* (2013.01); *A61K 38/08* (2013.01); *A61K 45/06* (2013.01); *C07D 231/56* (2013.01); *C07D 401/04* (2013.01); *C07D 401/14* (2013.01); *C07D 403/12* (2013.01); *C07D 405/14* (2013.01); *C07D 417/04* (2013.01)

(58) Field of Classification Search
None
See application file for complete search history.

(56) References Cited

U.S. PATENT DOCUMENTS

| | | | |
|---|---|---|---|
| 8,546,389 | B2 | 10/2013 | Halim et al. |
| 2012/0142686 | A1 | 6/2012 | Halim et al. |

FOREIGN PATENT DOCUMENTS

| | | |
|---|---|---|
| WO | WO 2008/141385 | 11/2008 |
| WO | WO 2011/153588 | 12/2011 |

OTHER PUBLICATIONS

International Preliminary Report on Patentability and Written Opinion in PCT/AU2013/000369 dated Oct. 14, 2014.
International Search Report for PCT/AU2013/000369 dated May 23, 2013.

*Primary Examiner* — Patrick Lewis
(74) *Attorney, Agent, or Firm* — B. Aaron Schulman, Esq.; Stites & Harbison, PLLC.

(57) ABSTRACT

The present invention relates to viral polymerase inhibitors of formula (I) or salts, N-oxides, solvates, hydrates, racemates, enantiomers or isomers thereof, processes for their preparation and their use in the treatment of Flaviviridae viral infections such as Hepatitis C virus (HCV) infections.

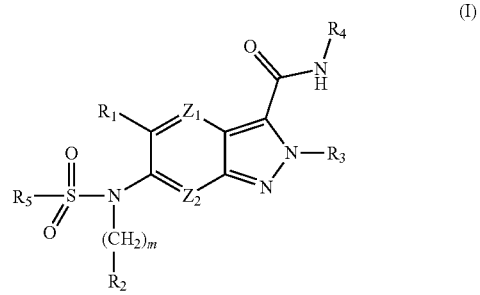

23 Claims, No Drawings

VIRAL POLYMERASE INHIBITORS

FIELD

The present invention relates to viral polymerase inhibitors, in particular inhibitors of viral polymerases within the Flaviviridae family such as hepatitis C virus (HCV), processes for their preparation and their use in the treatment of Flaviviridae viral infections such as Hepatitis C virus (HCV) infections.

BACKGROUND

The Flaviviridae are a group of positive single-stranded RNA viruses with a genome size from 9-15 kb. The Flaviviridae consist of various genera including: Hepaciviruses (this genus contains only one species, the Hepatitis C virus (HCV), which is composed of many genotypes and subtypes); Flaviviruses (this genus includes the Dengue virus, Japanese Tick-Borne and the Yellow Fever virus and there are some additional Flaviviruses that are unclassified) and Pestiviruses (this genus includes three serotypes of bovine viral diarrhoea virus, but no known human pathogens).

Hepatitis C virus (HCV) is a major cause of viral hepatitis and has infected more than 200 million people worldwide. Hepatitis C virus has a positive-strand RNA genome enclosed in a nucleocapsid and lipid envelope. The HCV genome is approximately 9.6 kb in length and encodes a polyprotein of about 3,000 amino acids. There are at least six major genotypes, which have different geographic distributions. In the United States (US), for example, genotypes 1a and 1b account for about 75% of cases, and genotypes 2 and 3 for 10-20% of cases. Significant differences are observed in the geographic distribution of HCV genotypes. For example, in Europe genotypes 2 and 3 comprise up to one half of cases whereas genotype 3 is thought to dominate in India. In addition, varied genotype distributions can be observed between countries in a particular region as well as in different areas of a given nation. In the US, HCV is the most common chronic blood-borne infection, affecting approximately 3.2 million persons. After infection with HCV, approximately 75-85% of people develop chronic infection, whilst 60-70% develop chronic liver disease. Of these, 5-20% go on to develop cirrhosis over a period of 20-30 years, and, finally, 1-5% succumb to the consequences of chronic infection (liver cancer/cirrhosis).

Until recently, the only treatment option for HCV was 24 or 48 weeks of combination therapy consisting of weekly injections of pegylated interferon (peg-IFN) and oral ribavirin for 24 or 48 weeks. The best treatment response is seen in patients with HCV genotypes 2 and 3, in whom sustained viral response (SVR) rates of approximately 80% can be achieved with 24 weeks of therapy. Patients with HCV genotype 1 remain the most difficult to treat, with SVR rates of approximately 40% after 48 weeks of therapy. In addition to the low response rates, combination peg-IFN/ribavirin therapy is limited by serious side effects, including fatigue, influenza-like symptoms, depression and suicide with peg-IFN, and haemolytic anaemia with ribavirin. Furthermore, peg-IFN/ribavirin therapy is contra-indicated in patients who have depression, anaemia, HCV-related decompensated cirrhosis, alcohol/substance abuse and autoimmune disorders or who are pregnant.

New treatment options for HCV became available in May 2011 with the US launch of the first direct-acting antiviral (DAA) HCV drugs, telaprevir (Vertex Pharmaceuticals) and boceprevir (Merck). Both drugs are protease inhibitors and are approved for the treatment of chronic HCV genotype 1 infection in combination with peg-IFN and ribavirin. Pivotal phase 3 trials demonstrated that the addition of telaprevir or boceprevir to peg-IFN/ribavirin therapy achieved shortened durations of therapy and potent viral suppression, with SVR rates approaching 75% in genotype 1 treatment-naive patients and 30% to 85% in treatment-experienced patients.

However, addition of a third drug to the treatment regimen has resulted in increased adverse events. Telaprevir is associated with an increased incidence of rash and anaemia, while boceprevir is associated with anaemia and dysgeusia. Triple therapy with telaprevir or boceprevir and peg-IFN/ribavirin remains unsuitable for those intolerant to or with contraindications to peg-IFN/ribavirin therapy.

Further, the majority of compounds that are currently in development have a limited spectrum of activity against the various HCV genotypes and, in many cases, are only active against HCV genotypes 1b and/or 1a.

The HCV genome possesses structural (core) and non-structural (NS2, NS3, NS4A, NS4B, NS5A and NS5B) proteins. The non-structural proteins are involved in viral genomic replication, with the initial synthesis of RNA carried out by NS5B RNA dependent RNA polymerase. The NS5B protein is a key target for anti-HCV therapy, as it is essential for HCV replication and has no human host equivalent. This protein has been well characterised and is a validated target for drug discovery.

HCV therapy is also anticipated to evolve towards oral multidrug therapy, in which combinations of different DAA drugs with complementary mechanisms of action serve to increase viral suppression and delay or prevent the emergence of resistance.

Due to the limited tolerability, efficacy, side effects and concern over the emergence of resistance there is an ongoing need to find alternative agents for the treatment of HCV, particularly with targeted mechanisms of action such as NS5B inhibitors.

SUMMARY

The inventors have found a new class of NS5B polymerase inhibitors for the treatment of HCV infections.

Compounds of the present invention are therefore considered to be useful in treating and preventing hepatitis C infections when used on their own or in combination with one or more other antiviral agents such as ribavirin, an antiviral nucleoside, polymerase inhibitor, protease inhibitor and/or inhibitor of viral entry, assembly or egress. The combination may also additionally comprise at least one immunomodulatory agent for example an interferon or interferon derivative and/or an inhibitor of inosine-5'-monophosphate dehydrogenase (IMPDH).

It is also believed that compounds of the invention will be efficacious in combination with at least one other DAA with a different mechanism of action and a complementary resistance profile (for example an NS5A inhibitor, a nucleoside or nucleotide NS5B inhibitor or a NS3 protease inhibitor) thereby offering an alternative treatment regime for patients not eligible for or treatable with the recently approved triple combination therapy.

According to a first aspect there is provided a compound of formula (I), salts, N-oxides, solvates, hydrates, racemates, enantiomers or diastereomers thereof:

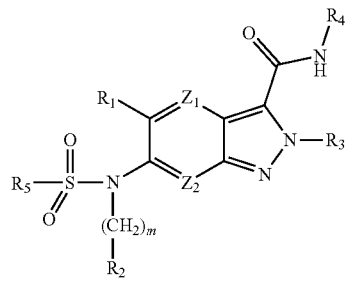

(I)

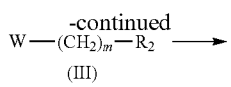

(III)

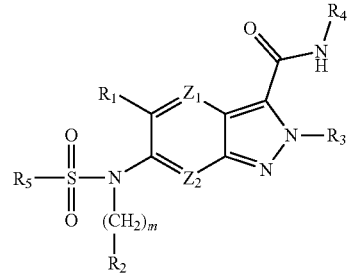

(I)

wherein
$Z_1$ and $Z_2$ are each independently selected from C—H, C-halo, C—$C_{1-4}$alkyl, C—$C_{1-4}$alkylhalo, C—$C_{1-4}$alkoxy, C—$C_{1-4}$alkoxyhalo and N;
$R_1$ is selected from H, $C_{1-6}$alkyl, $C_{2-6}$alkenyl, $C_{2-6}$alkynyl, $C_{1-6}$alkoxy, halo, $C_{1-4}$alkylhalo, $C_{1-4}$alkoxyhalo, $C_{3-7}$cycloalkyl, $C_{3-7}$cycloalkenyl, 5-6-membered heterocyclyl and 5-6 membered heteroaryl and wherein alkyl, alkenyl, alkynyl, alkoxy, cycloalkyl, heterocyclyl and heteroaryl in each occurrence may be optionally substituted;
$R_2$ is an optionally substituted 4-membered heterocyclic ring;
$R_3$ is selected from aryl, aryl-X-aryl, aryl-X-heteroaryl, heteroaryl, heteroaryl-X-heteroaryl, and heteroaryl-X-aryl wherein X is $[C(R_5)_2]_p$, O, S, S(=O), $SO_2$, $NR_5$, C=O, $CF_2$, C(=O)$NR_5$ or $NR_5$C(=O) wherein p is 1, 2 or 3 and wherein aryl and heteroaryl in each occurrence may be optionally substituted and further wherein aryl is preferably phenyl and heteroaryl is preferably 5-6-membered heteroaryl;
$R_4$ is H, $C_{1-4}$alkyl, $C_{2-4}$alkenyl, $C_{2-4}$alkynyl, or $C_{3-7}$cycloalkyl preferably $C_{1-4}$alkyl;
$R_5$ in each occurrence is independently H or optionally substituted $C_{1-6}$alkyl;
m represents an integer selected from 0, 1, 2, 3, 4, 5 and 6; and
each ($CH_2$) moiety when present may be independently optionally substituted with one or two substituents;
and further when m is an integer selected from 1, 2, 3, 4, 5 and 6 then one or more ($CH_2$) may be replaced with O, C=O, NH, optionally substituted $NC_{1-6}$alkyl, S, S=O or $SO_2$.

In a preferred embodiment $R_2$ is an optionally substituted azetidine or an optionally substituted oxetane. Optionally substituted oxetanes are particularly preferred.

According to a second aspect there is provided a process for producing the compound of formula (I) defined above comprising the step of coupling a compound of formula (II):

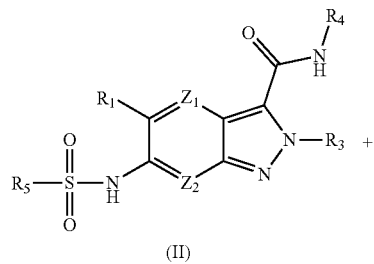

(II)

with a compound of general formula (III) under coupling conditions;
wherein
W is hydroxyl, mesylate, tosylate, triflate or halo; and
$Z_1$, $Z_2$, $R_1$, $R_2$, $R_3$, $R_4$, $R_5$ and $(CH_2)_m$ are as previously defined.

Alternatively, the moiety $R_2$ may be introduced post-coupling of a suitable precursor moiety to a compound of formula (II), for example, a precursor containing a diol or alkene group which is subsequently functionalised to the desired $R_2$ moiety under suitable ring forming conditions.

Some of the compounds of formula (II) are believed to be novel and also fall within the scope of the present invention, particularly compounds in which $R_3$ is an optionally substituted 2-pyridyl.

The compounds of formula (I) are inhibitors of HCV. In particular, the compounds of formula (I) inhibit RNA synthesis by the RNA dependent RNA polymerase of HCV (the NS5B protein encoded by HCV). NS5B inhibitors have been clinically validated as potential antiviral agents for the treatment of HCV infection.

According to a third aspect, there is provided a pharmaceutical agent comprising the compound of formula (I) or salts, N-oxides, solvates, hydrates, racemates, enantiomers or diastereomers thereof as defined above, optionally in combination with another HCV antiviral agent.

There is also provided use of the compound of formula (I) or salts, N-oxides, solvates, hydrates, racemates, enantiomers or diastereomers thereof as defined above as a pharmaceutical agent, optionally in combination with another HCV antiviral agent.

There is further provided the compound of formula (I) or salts, N-oxides, solvates, hydrates, racemates, enantiomers or diastereomers thereof as defined above for use as a pharmaceutical agent, optionally in combination with another HCV antiviral agent.

The pharmaceutical agent may be an antiviral agent.

According to a fourth aspect, there is provided a viral polymerase inhibitor in particular a HCV polymerase inhibitor such as a NS5B inhibitor comprising the compound of formula (I) or salts, N-oxides, solvates, hydrates, racemates, enantiomers or diastereomers thereof as defined above, optionally in combination with another HCV antiviral agent.

There is also provided use of the compound of formula (I) or salts, N-oxides, solvates, hydrates, racemates, enantiomers or diastereomers thereof as defined above as a viral polymerase inhibitor in particular a HCV polymerase inhibitor such as a NS5B inhibitor, optionally in combination with another HCV antiviral agent.

There is further provided the compound of formula (I) or salts, N-oxides, solvates, hydrates, racemates, enantiomers or diastereomers thereof as defined above for use as a viral polymerase inhibitor in particular a HCV polymerase inhibitor such as a NS5B inhibitor, optionally in combination with another HCV antiviral agent.

The compound of formula (I) or salts, N-oxides, solvates, hydrates, racemates, enantiomers or diastereomers thereof as may be administered in the form of a pharmaceutical composition together with a pharmaceutically acceptable carrier, optionally in combination with another HCV antiviral agent.

According to a fifth aspect, there is provided a pharmaceutical composition comprising the compound of formula (I) or salts, N-oxides, solvates, hydrates, racemates, enantiomers or diastereomers thereof and a pharmaceutically acceptable carrier.

According to one embodiment, the pharmaceutical composition additionally comprises a therapeutically effective amount of one or more antiviral agents such as at least one other HCV antiviral agent.

According to a sixth aspect, there is provided a method for the treatment of a Flaviviridae viral infection such as a HCV infection which comprises administering an effective amount of the compound of formula (I) or salts, N-oxides, solvates, hydrates, racemates, enantiomers or diastereomers thereof as defined above or the pharmaceutical agent or pharmaceutical composition defined above, optionally in combination with another HCV antiviral agent to a subject in need thereof.

There is also provided use of the compound of formula (I) or salts, N-oxides, solvates, hydrates, racemates, enantiomers or diastereomers thereof as defined above or the pharmaceutical agent or pharmaceutical composition as defined above in the manufacture of a medicament for use in the treatment of a Flaviviridae viral infection such as a HCV infection, optionally in combination with another HCV antiviral agent.

There is further provided use of the compound of formula (I) or salts, N-oxides, solvates, hydrates, racemates, enantiomers or diastereomers thereof as defined above or the pharmaceutical agent or pharmaceutical composition as defined above, optionally in combination with another HCV antiviral agent in the treatment of a Flaviviridae viral infection such as a HCV infection.

There is still further provided the compound of the formula (I) or salts, N-oxides, solvates, hydrates, racemates, enantiomers or diastereomers thereof as defined above or the pharmaceutical agent or pharmaceutical composition defined above, optionally in combination with another HCV antiviral agent for use in the treatment of a Flaviviridae viral infection such as a HCV infection.

According to a seventh aspect, there is provided a method of inhibiting the RNA-dependent RNA polymerase activity of the enzyme NS5B, encoded by HCV, comprising exposing the enzyme NS5B to an effective amount of the compound of formula (I) or salts, N-oxides, solvates, hydrates, racemates, enantiomers or diastereomers thereof as defined above, optionally in combination with another HCV antiviral agent.

According to an eighth aspect, there is provided a method of inhibiting HCV replication comprising exposing a cell infected with HCV to an effective amount of the compound of formula (I) or pharmaceutically acceptable salts, N-oxides, solvates, hydrates, racemates, enantiomers or diastereomers thereof as defined above, optionally in combination with another HCV antiviral agent.

DETAILED DESCRIPTION

The present invention is predicated on the discovery of a new class of compounds that have been shown to inhibit viral polymerases, more particularly NS5B polymerases. Accordingly in one embodiment the compounds of formula (I) are useful in the treatment of Flaviviridae viral infections, particularly, hepatitis C (HCV).

Applicant's earlier filed U.S. Ser. No. 13/278,021 and WO2012/051659 (PCT/AU2011/001336) are directed to a structurally related class of compounds. However, the compounds of the present invention are not specifically described therein and further have demonstrated good activity, generally in the nanomolar range(s) of the earlier applications.

The compounds are also believed to possess one or more advantageous pharmaceutical properties including solubility and/or metabolic stability.

DEFINITIONS

Unless otherwise herein defined, the following terms will be understood to have the general meanings which follow.

The term "$C_{1-6}$alkyl" refers to optionally substituted straight chain or branched chain hydrocarbon groups having from 1 to 6 carbon atoms. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. "$C_{1-4}$alkyl" and "$C_{1-3}$alkyl" including methyl, ethyl, propyl, isopropyl, n-butyl, isobutyl, sec-butyl and tert-butyl are preferred with methyl being particularly preferred.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl. Unless the context requires otherwise, the term "$C_{2-6}$ alkenyl" also encompasses alkenyl groups containing one less hydrogen atom such that the group is attached via two positions i.e. divalent. "$C_{2-4}$alkenyl" and "$C_{2-3}$alkenyl" including ethenyl, propenyl and butenyl are preferred with ethenyl being particularly preferred.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl and the like. Unless the context indicates otherwise, the term "$C_{2-6}$alkynyl" also encompasses alkynyl groups containing one less hydrogen atom such that the group is attached via two positions i.e. divalent. $C_{2-3}$alkynyl is preferred.

The term "$C_{3-8}$cycloalkyl" refers to non-aromatic cyclic groups having from 3 to 8 carbon atoms, including cyclopropyl, cyclobutyl, cyclopentyl, cyclohexyl, cycloheptyl and cyclooctyl. It will be understood that cycloalkyl groups may be saturated such as cyclohexyl or unsaturated such as cyclohexenyl. $C_3$-6cycloalkyl such as cyclopropyl, cyclobutyl, cyclopentyl and cyclohexyl are preferred.

The terms "hydroxy" and "hydroxyl" refer to the group —OH.

The term "oxo" refers to the group =O.

The term "$C_{1-6}$alkoxy" refers to an alkyl group as defined above covalently bound via an O linkage containing 1 to 6 carbon atoms, such as methoxy, ethoxy, propoxy, isoproxy, butoxy, tert-butoxy and pentoxy. "$C_{1-4}$alkoxy" and "$C_{1-3}$ alkoxy" including methoxy, ethoxy, propoxy and butoxy are preferred with methoxy being particularly preferred.

The term "$C_{1-6}$alkylhalo" refers to a $C_{1-6}$alkyl which is substituted with one or more halogens. $C_{1-3}$alkylhalo groups are preferred, such as for example, —CHF$_2$ and —CF$_3$.

The term "$C_{1-6}$alkoxyhalo" refers to a $C_{1-6}$alkoxy which is substituted with one or more halogens. $C_{1-3}$alkoxyhalo groups are preferred, such as for example, —OCHF$_2$ and —OCF$_3$. The term "carboxylate" or "carboxyl" refers to the group —COO— or —COOH.

The term "ester" refers to a carboxyl group having the hydrogen replaced with, for example a $C_{1-6}$alkyl group ("carboxyl$C_{1-6}$alkyl" or "alkylester"), an aryl or aralkyl group ("arylester" or "aralkylester") and so on. CO$_2$C$_{1-3}$alkyl groups are preferred, such as for example, methylester (CO$_2$Me), ethylester (CO$_2$Et) and propylester (CO$_2$Pr) and includes reverse esters thereof (e.g. —OCOMe, —OCOEt and —OCOPr).

The term "cyano" refers to the group —CN.

The term "nitro" refers to the group —NO$_2$.

The term "amino" refers to the group —NH$_2$.

The term "substituted amino" or "secondary amino" refers to an amino group having a hydrogen replaced with, for example a $C_{1-6}$alkyl group ("$C_{1-6}$alkylamino"), an aryl or aralkyl group ("arylamino", "aralkylamino") and so on. $C_{1-3}$alkylamino groups are preferred, such as for example, methylamino (NHMe), ethylamino (NHEt) and propylamino (NHPr).

The term "disubstituted amino" or "tertiary amino" refers to an amino group having the two hydrogens replaced with, for example a $C_{1-6}$alkyl group, which may be the same or different ("dialkylamino"), an aryl and alkyl group ("aryl (alkyl)amino") and so on. Di($C_{1-3}$alkyl)amino groups are preferred, such as for example, dimethylamino (NMe$_2$), diethylamino (NEt$_2$), dipropylamino (NPr$_2$) and variations thereof (e.g. N(Me)(Et) and so on).

The term "acyl" or "aldehyde" refers to the group —C(=O)H.

The term "substituted acyl" or "ketone" refers to an acyl group having a hydrogen replaced with, for example a $C_{1-6}$alkyl group ("$C_{1-6}$alkylacyl" or "alkylketone" or "ketoalkyl"), an aryl group ("arylketone"), an aralkyl group ("aralkylketone) and so on. $C_{1-3}$alkylacyl groups are preferred.

The term "amido" or "amide" refers to the group —C(O)NH$_2$.

The term "aminoacyl" refers to the group —NHC(O)H.

The term "substituted amido" or "substituted amide" refers to an amido group having a hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di($C_{1-6}$alkyl)amido" or "di($C_{1-6}$alkyl)amide"), an aralkyl and alkyl group ("alkyl (aralkyl)amido") and so on. Di($C_{1-3}$alkyl)amide groups are preferred, such as for example, dimethylamide (—C(O)NMe$_2$), diethylamide (—C(O)NEt$_2$) and dipropylamide ((—C(O)NPr$_2$) and variations thereof (e.g. —C(O)N(Me)Et and so on) and includes reverse amides thereof.

The term "thiol" refers to the group —SH.

The term "$C_{1-6}$alkylthio" refers to a thiol group having the hydrogen replaced with a $C_{1-6}$alkyl group. $C_{1-3}$alkylthio groups are preferred, such as for example, thiolmethyl, thiolethyl and thiolpropyl.

The term "thioxo" refers to the group =S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on. $C_{1-3}$alkylsulfinyl groups are preferred, such as for example, —SOmethyl, —SOethyl and —SOpropyl.

The term "sulfonyl" refers to the group —SO$_2$H.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —SO$_2$Me, —SO$_2$Et and —SO$_2$Pr.

The term "sulfonylamido" or "sulfonamide" refers to the group —SO$_2$NH$_2$.

The term "substituted sulfonamido" or "substituted sulphonamide" refers to an sulfonylamido group having a hydrogen replaced with, for example a $C_{1-6}$alkyl group ("sulfonylamido$C_{1-6}$alkyl"), an aryl ("arylsulfonamide"), aralkyl ("aralkylsulfonamide") and so on. Sulfonylamido-$C_{1-3}$alkyl groups are preferred, such as for example, —SO$_2$NHMe, —SO$_2$NHEt and —SO$_2$NHPr and includes reverse sulfonamides thereof (e.g. —NHSO$_2$Me, —NHSO$_2$Et and —NHSO$_2$Pr).

The term "disubstituted sufonamido" or "disubstituted sulphonamide" refers to an sulfonylamido group having the two hydrogens replaced with, for example a $C_{1-6}$alkyl group, which may be the same or different ("sulfonylamidodi-($C_{1-6}$alkyl)"), an aralkyl and alkyl group ("sulfonamido (aralkyl)alkyl") and so on. Sulfonylamidodi($C_{1-3}$alkyl) groups are preferred, such as for example, —SO$_2$NMe$_2$, —SO$_2$NEt$_2$ and —SO$_2$NPr$_2$ and variations thereof (e.g. —SO$_2$N(Me)Et and so on) and includes reserve sulfonamides thereof.

The term "sulfate" refers to the group OS(O)$_2$OH and includes groups having the hydrogen replaced with, for example a $C_{1-6}$alkyl group ("alkylsulfates"), an aryl ("arylsulfate"), an aralkyl ("aralkylsulfate") and so on. $C_{1-3}$sulfates are preferred, such as for example, OS(O)$_2$OMe, OS(O)$_2$OEt and OS(O)$_2$OPr.

The term "sulfonate" refers to the group SO$_3$H and includes groups having the hydrogen replaced with, for example a $C_{1-6}$alkyl group ("alkylsulfonate"), an aryl ("arylsulfonate"), an aralkyl ("aralkylsulfonate") and so on. $C_{1-3}$sulfonates are preferred, such as for example, SO$_3$Me, SO$_3$Et and SO$_3$Pr.

The term "aryl" refers to a carbocyclic (non-heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred.

The term "alkylaryl" refers to $C_{1-6}$alkylaryl such as benzyl.

The term "alkoxyaryl" refers to $C_{1-6}$alkyloxyaryl such as benzyloxy.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms each heteroatom being independently selected from O, S and N.

In this context, the prefixs 3-, 4-, 5-, 6-, 7-, 8-, 9- and 10-membered denote the number of ring atoms, or range of ring atoms, whether carbon atoms or heteroatoms. For example, the term "3-10 membered heterocylyl", as used herein, pertains to a heterocyclyl group having 3, 4, 5, 6, 7, 8, 9 or 10 ring atoms. Examples of heterocylyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, napthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from the group consisting of N, S and O.

Non-aromatic heterocyclyls may be 3-7 membered monocyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

The term "halo" refers to fluoro, chloro, bromo or iodo.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case of heterocycles containing N may also include but are not limited to $C_{1-6}$alkyl i.e. N—$C_{1-3}$alkyl, more preferably methyl particularly N-methyl.

It will be understood that suitable derivatives of aromatic heterocyclyls containing nitrogen include N-oxides thereof.

Compounds

The present invention relates to compounds of formula (I), salts, N-oxides, solvates, hydrates, racemates, enantiomers or diastereomers thereof as defined above.

In one embodiment, there is provided a compound of formula (Ia), salts, N-oxides, solvates, hydrates, racemates, enantiomers or isomers thereof

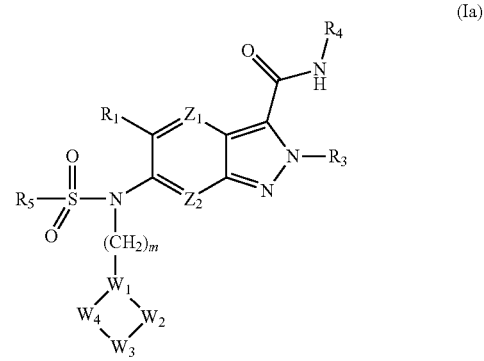

(Ia)

wherein $Z_1$, $Z_2$, $R_1$, $R_3$, $R_4$, $R_5$ and $(CH_2)_m$ are as previously defined;
$W_1$ is $CR^a$ or N;
$W_2$, $W_3$ and $W_4$ are each independently selected from O, $NR^b$, S, S=O, $SO_2$, C=O or $CR^cR^d$; and
$R^a$, $R^b$, $R^c$ and $R^d$ are each independently selected from H or an optional substituent as previously defined,
with the proviso that one of $W_1$, $W_2$, $W_3$ and $W_4$ is a heteroatom selected from O, $NR^b$ and S, preferably O or NR$^b$ and the three remaining are independently CR$^a$ in the case of W$_1$ and CR$^c$R$^d$ in the case of any one of W$_2$, W$_3$ and W$_4$.

In one embodiment W$_1$ is CR$^a$, W$_2$ is O or NR$^b$ and W$_3$ and W$_4$ are independently CR$^c$R$^d$.

In another embodiment W$_1$ is CR$^a$, W$_3$ is O or NR$^b$ and W$_2$ and W$_4$ are independently CR$^c$R$^d$.

In one embodiment W$_1$ is N and W$_2$, W$_3$ and W$_4$ are each independently CR$^c$R$^d$.

In one embodiment R$^a$, R$^b$, R$^c$ and R$^d$ are each independently selected from H, halo, optionally substituted C$_{1-6}$alkyl, haloC$_{1-3}$alkyl including CHF$_2$ and CF$_3$, optionally substituted C$_{1-3}$alkoxy, haloC$_{1-3}$alkoxy including OCHF$_2$ and OCF$_3$, OH, =O, C(=O)C$_{1-3}$alkyl, CN, NO$_2$, NH$_2$, optionally substituted NHC$_{1-6}$alkyl, optionally substituted N(C$_{1-6}$alkyl)$_2$, optionally substituted amides of general formula NHC(=O)C$_{1-6}$alkyl, CO$_2$H and optionally substituted esters of general formula C(=O)OC$_{1-6}$alkyl.

In one embodiment R$^a$, R$^b$, R$^c$ and R$^d$ are independently selected from H, F, optionally substituted C$_{1-3}$alkyl (preferably methyl which may be further optionally substituted with NHC(=O)OC$_{1-4}$alkyl, preferably NHC(=O)O-tert-butyl), C(=O)CH$_3$, CHF$_2$, CF$_3$, OH and methoxy, preferably H, F, methyl, OH and methoxy, even more preferably H and methyl.

In one embodiment (CH$_2$)$_m$ represents an optionally substituted methylenyl (i.e. m=1), ethylenyl (i.e. m=2) or propylenyl (i.e. m=3) moiety, preferably m is 1 or 2.

In one embodiment each (CH$_2$)$_m$ when present may be independently optionally substituted with one or two optional substituents as previously defined and preferably selected from the group consisting of halo, optionally substituted C$_{1-6}$alkyl, optionally substituted C$_{2-6}$alkenyl, haloC$_{1-3}$alkyl, OH, =O, optionally substituted C$_{1-6}$alkoxy, haloC$_{1-3}$alkoxyl, CO$_2$H, optionally substituted esters of general formula C(=O)OC$_{1-6}$alkyl, CN, NO$_2$, NH$_2$, NHC$_{1-3}$alkyl, N(C$_{1-3}$alkyl)$_2$, optionally substituted amides of general formula NHC(=O)C$_{1-6}$alkyl, an optionally substituted C$_{3-7}$cycloalkyl, an optionally substituted C$_{6-10}$aryl and an optionally substituted 4-10-membered heterocyclyl.

C$_{1-3}$alkyl particularly methyl, halo particularly fluoro and C$_{1-3}$alkoxy particularly methoxy, are preferred optional substituents for (CH$_2$) when present with methyl and fluoro being most preferred.

In one embodiment Z$_1$ and Z$_2$ are C—H; R$_1$ is selected from optionally substituted C$_{1-3}$alkyl, C$_{1-3}$alkoxyl and C$_{3-5}$cycloalkyl, preferably cyclopropyl; R$_3$ is an optionally substituted phenyl or an optionally substituted 6-membered heteroaryl ring selected from pyridyl, pyridazinyl, pyrimidinyl and pyrazinyl, preferably R$_3$ is optionally substituted phenyl or pyridyl with C$_{1-4}$alkyl and halo being particularly preferred optional substituents and methyl or Cl being most preferred; R$_4$ is an optionally substituted C$_{1-6}$alkyl, preferably C$_{1-3}$alkyl and more preferably is unsubstituted methyl; R$_5$ is optionally substituted C$_{1-6}$alkyl preferably C$_{1-3}$alkyl optionally substituted with halo such as CF$_3$ or CHF$_2$ with methyl being particularly preferred; m is an integer selected from 0, 1, 2 or 3, preferably 1, 2 or 3, even more preferably m is 2; and each —(CH$_2$)— when present is independently optionally substituted with one or two substituents as previously defined preferably independently selected from halo, C$_{1-4}$alkyl, haloC$_{1-3}$alkyl and C$_{1-3}$alkoxy.

In one embodiment the compound is of formula (I) and is selected from the group consisting of:

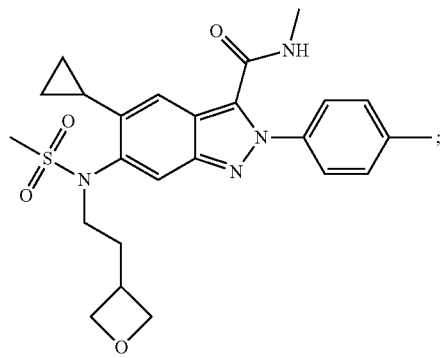

3

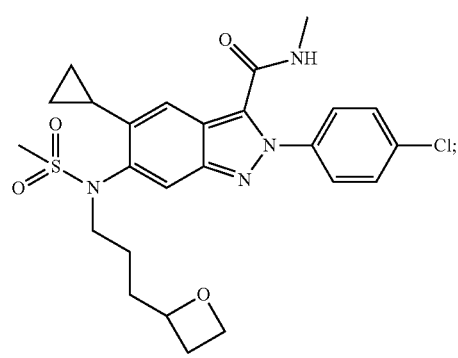

4

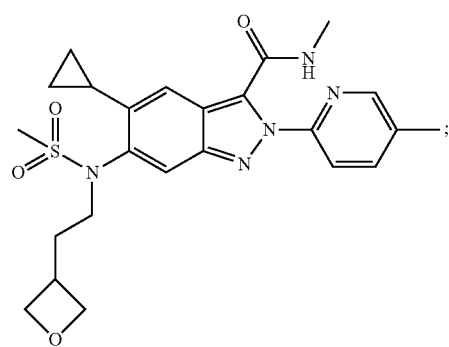

5

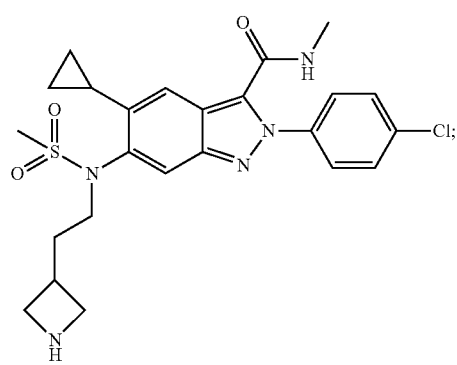

6

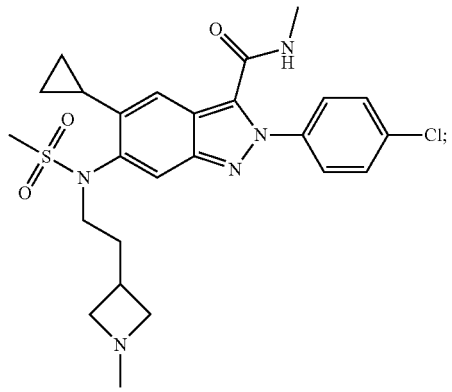
7
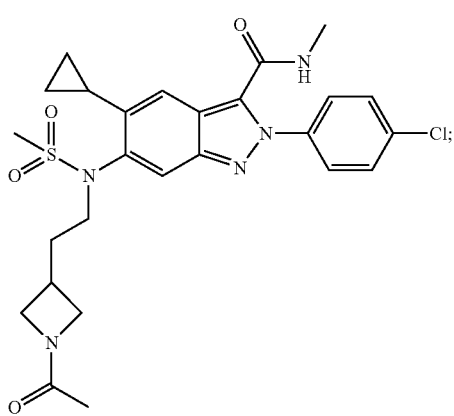
8
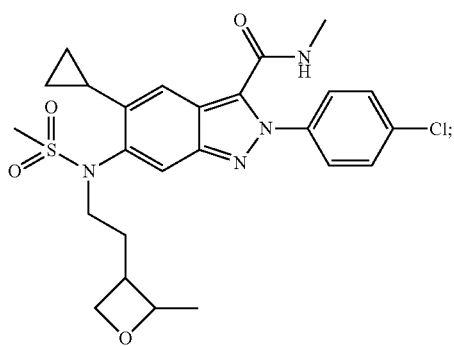
9
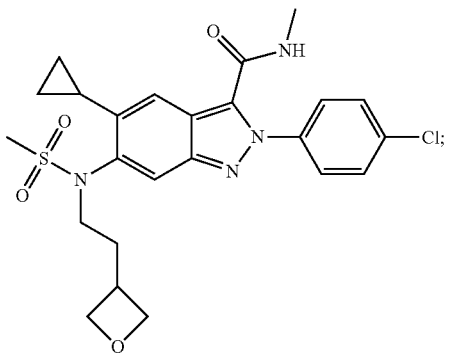
10
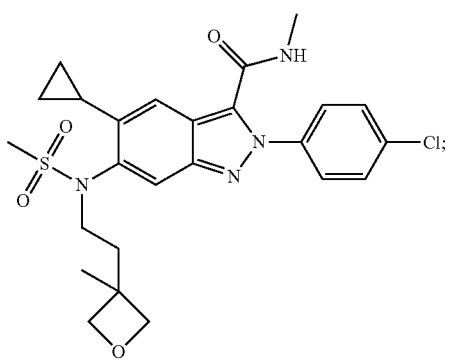
11
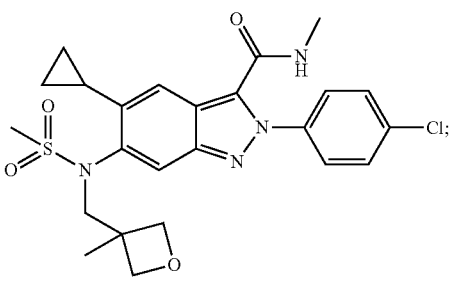
12
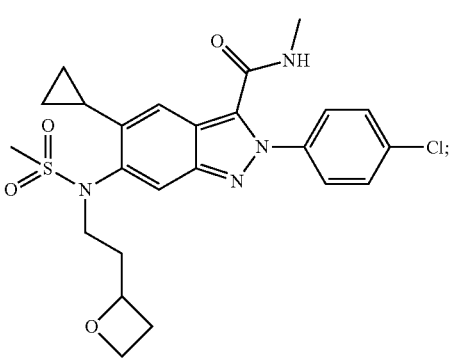
13
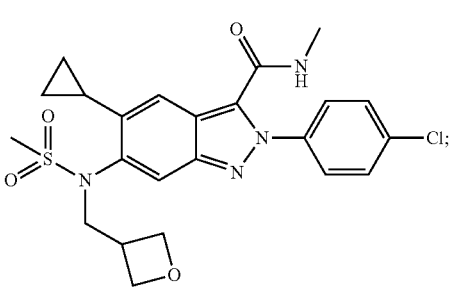
14
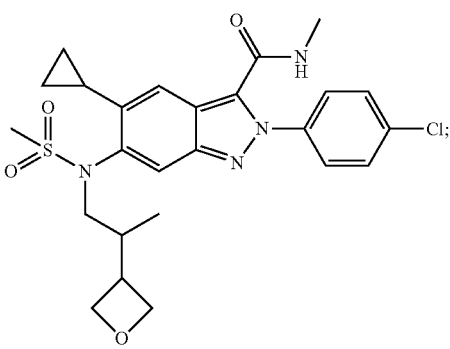
15

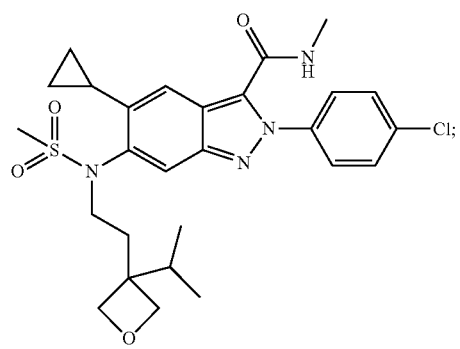
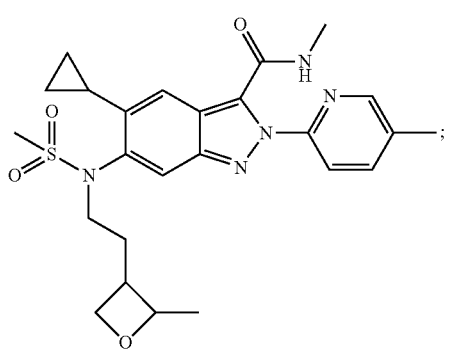
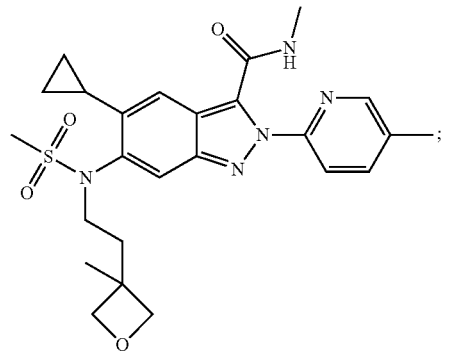
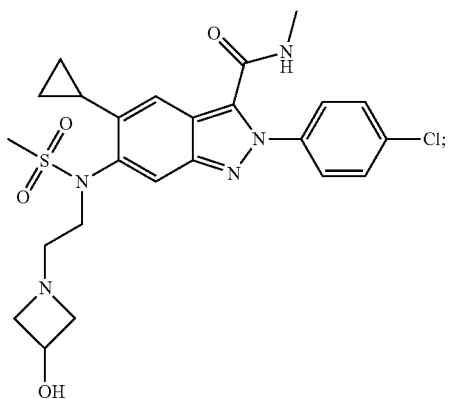
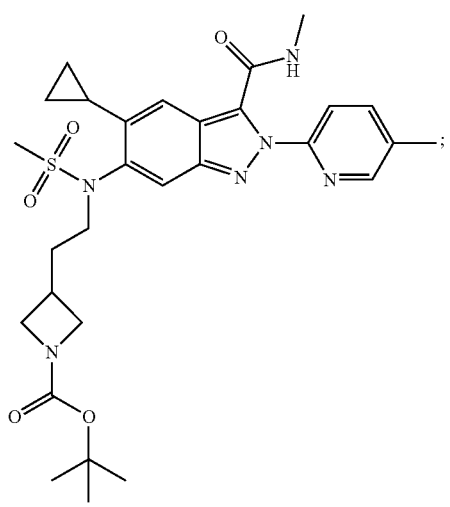

-continued

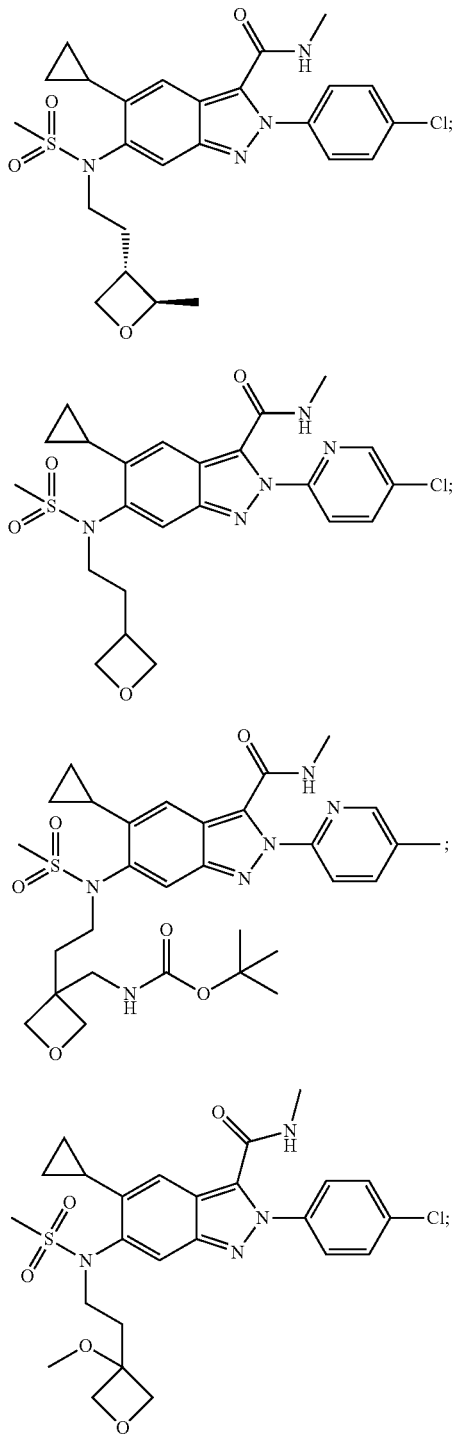

and salts, N-oxides, solvates, hydrates, racemates, enantiomers or diastereomers thereof wherein the compounds are named as follows:

3) 5-cyclopropyl-N-methyl-2-(4-methylphenyl)-6-{(methylsulfonyl)[2-(oxetan-3-yl)ethyl]amino}-2H-indazole-3-carboxamide;
4) 2-(4-chlorophenyl)-5-cyclopropyl-N-methyl-6-{(methylsulfonyl)[3-(oxetan-2-yl)propyl]amino}-2H-indazole-3-carboxamide;
5) 5-cyclopropyl-N-methyl-2-(5-methylpyridin-2-yl)-6-{(methylsulfonyl)[2-(oxetan-3-yl)ethyl]amino}-2H-indazole-3-carboxamide;
6) 6-{[2-(azetidin-3-yl)ethyl](methylsulfonyl)amino}-2-(4-chlorophenyl)-5-cyclopropyl-N-methyl-2H-indazole-3-carboxamide;
7) 2-(4-chlorophenyl)-5-cyclopropyl-N-methyl-6-{[2-(1-methylazetidin-3-yl)ethyl](methylsulfonyl)amino}-2H-indazole-3-carboxamide;
8) 6-{[2-(1-acetylazetidin-3-yl)ethyl](methylsulfonyl)amino}-2-(4-chlorophenyl)-5-cyclopropyl-N-methyl-2H-indazole-3-carboxamide;
9) 2-(4-chlorophenyl)-5-cyclopropyl-N-methyl-6-{[2-(2-methyloxetan-3-yl)ethyl](methylsulfonyl)amino}-2H-indazole-3-carboxamide;
10) 2-(4-chlorophenyl)-5-cyclopropyl-N-methyl-6-{(methylsulfonyl)[2-(oxetan-3-yl)ethyl]amino}-2H-indazole-3-carboxamide;
11) 2-(4-chlorophenyl)-5-cyclopropyl-N-methyl-6-{[2-(3-methyloxetan-3-yl)ethyl](methylsulfonyl)amino}-2H-indazole-3-carboxamide;
12) 2-(4-chlorophenyl)-5-cyclopropyl-N-methyl-6-{[(3-methyloxetan-3-yl)methyl](methylsulfonyl)amino}-2H-indazole-3-carboxamide;
13) 2-(4-chlorophenyl)-5-cyclopropyl-N-methyl-6-{(methylsulfonyl)[2-(oxetan-2-yl)ethyl]amino}-2H-indazole-3-carboxamide;
14) 2-(4-chlorophenyl)-5-cyclopropyl-N-methyl-6-[(methylsulfonyl)(oxetan-3-ylmethyl)amino]-2H-indazole-3-carboxamide;
15) 2-(4-chlorophenyl)-5-cyclopropyl-N-methyl-6-{(methylsulfonyl)[2-(oxetan-3-yl)propyl]amino}-2H-indazole-3-carboxamide;
16) 2-(4-chlorophenyl)-5-cyclopropyl-N-methyl-6-[(methylsulfonyl){2-[3-(propan-2-yl)oxetan-3-yl]ethyl}amino]-2H-indazole-3-carboxamide;
17) 3,5-anhydro-1-{[2-(4-chlorophenyl)-5-cyclopropyl-3-(methylcarbamoyl)-2H-indazol-6-yl](methylsulfonyl)amino}-1,2,4-trideoxy-4-methylpentitol;
18) 2-(4-chlorophenyl)-5-cyclopropyl-6-{[2-fluoro-2-(oxetan-3-yl)ethyl](methylsulfonyl)amino}-N-methyl-2H-indazole-3-carboxamide;
19) tert-butyl 3-(2-{[2-(4-chlorophenyl)-5-cyclopropyl-3-(methylcarbamoyl)-2H-indazol-6-yl](methylsulfonyl)amino}ethyl)azetidine-1-carboxylate;
20) 5-cyclopropyl-N-methyl-6-{[2-(2-methyloxetan-3-yl)ethyl](methylsulfonyl)amino}-2-(5-methylpyridin-2-yl)-2H-indazole-3-carboxamide;
21) 5-cyclopropyl-N-methyl-6-{[2-(3-methyloxetan-3-yl)ethyl](methylsulfonyl)amino}-2-(5-methylpyridin-2-yl)-2H-indazole-3-carboxamide;
22) 2-(4-chlorophenyl)-5-cyclopropyl-6-[2-(3-hydroxyazetidin-1-yl)ethyl-methylsulfonyl-amino]-N-methyl-indazole-3-carboxamide;
24) tert-butyl 3-[2-[[5-cyclopropyl-3-(methylcarbamoyl)-2-(5-methyl-2-pyridyl)indazol-6-yl]-methylsulfonyl-amino]ethyl]azetidine-1-carboxylate;
25) 6-[2-(1-acetylazetidin-3-yl)ethyl-methylsulfonyl-amino]-5-cyclopropyl-N-methyl-2-(5-methyl-2-pyridyl)indazole-3-carboxamide;
26) 2-(4-chlorophenyl)-5-cyclopropyl-6-[2-(3-fluorooxetan-3-yl)ethyl-m ethylsulfonyl-amino]-N-methyl-indazole-3-carboxamide;
27) tert-butyl 3-[2-[[2-(4-chlorophenyl)-5-cyclopropyl-3-(methylcarbamoyl)indazol-6-yl]-methylsulfonyl-amino]ethyl]-3-methoxy-azetidine-1-carboxylate;

28) 5-cyclopropyl-6-[2-(3-methoxyoxetan-3-yl)ethyl-methylsulfonyl-amino]-N-methyl-2-(5-methyl-2-pyridyl)indazole-3-carboxamide;
29) 2-(4-chlorophenyl)-5-cyclopropyl-6-[2-(3-methoxyazetidin-3-yl)ethyl-methylsulfonyl-amino]-N-methyl-indazole-3-carboxamide;
30) 6-[2-(1-acetyl-3-methoxy-azetidin-3-yl)ethyl-methylsulfonyl-amino]-2-(4-chlorophenyl)-5-cyclopropyl-N-methyl-indazole-3-carboxamide;
31) 2-(4-chlorophenyl)-5-cyclopropyl-N-methyl-6-[2-[-2-methyloxetan-3-yl]ethyl-methylsulfonyl-amino]indazole-3-carboxamide;
32) 2-(4-chlorophenyl)-5-cyclopropyl-N-methyl-6-[{2-[(2S,3R)-2-methyloxetan-3-yl]ethyl}(methylsulfonyl)amino]-2H-indazole-3-carboxamide;
33) 2-(4-chlorophenyl)-5-cyclopropyl-N-methyl-6-[{2-[(2R,3S)-2-methyloxetan-3-yl]ethyl}(methylsulfonyl)amino]-2H-indazole-3-carboxamide;
34) 2-(5-chloro-2-pyridyl)-5-cyclopropyl-N-methyl-6-[methylsulfonyl-[2-(oxetan-3-yl)ethyl]amino]indazole-3-carboxamide;
35) tert-butyl N-[[3-[2-[[5-cyclopropyl-3-(methylcarbamoyl)-2-(5-methyl-2-pyridyl)indazol-6-yl]-methylsulfonyl-amino]ethyl]oxetan-3-yl]methyl]carbamate; and
36) 2-(4-chlorophenyl)-5-cyclopropyl-6-[2-(3-methoxyoxetan-3-yl)ethyl-m ethylsulfonyl-amino]-N-methyl-indazole-3-carboxamide.

In one embodiment the compound is of formula (II) and selected from the group consisting of:

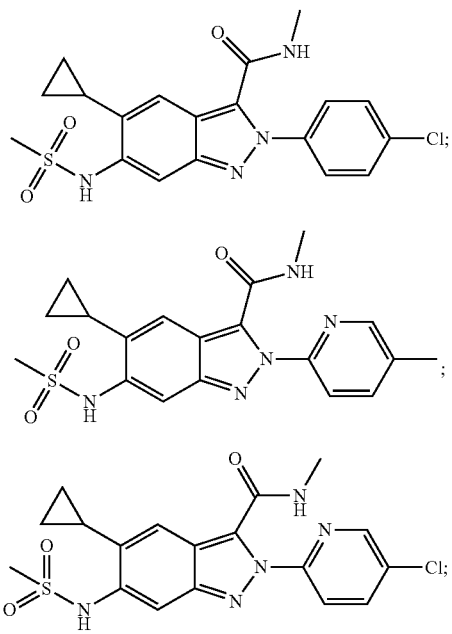

and
salts, N-oxides, solvates, hydrates, racemates, enantiomers or diastereomers thereof wherein the compounds are named as follows:
1) 2-(4-chlorophenyl)-5-cyclopropyl-N-methyl-6-[(methylsulfonyl)amino]-2H-indazole-3-carboxamide;
2) 5-cyclopropyl-N-methyl-2-(5-methylpyridin-2-yl)-6-[(methylsulfonyl)amino]-2H-indazole-3-carboxamide; and
23) 2-(5-chloro-2-pyridyl)-5-cyclopropyl-6-(methanesulfonamido)-N-methyl-indazole-3-carboxamide.

The compounds of the invention may also be prepared as salts which are pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulfuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulfonic, trihalomethanesulfonic, toluenesulfonic, benzenesulfonic, isethionic, salicylic, sulphanilic, aspartic, glutamic, edetic, stearic, palmitic, oleic, lauric, pantothenic, tannic, ascorbic, valeric and orotic acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the compounds and methods provided herein.

Additionally, the compounds of the present invention can exist in unsolvated as well as solvated forms with pharmaceutically acceptable solvents such as water, ethanol, and the like. The solvated forms of the compounds of the present invention are also considered to be disclosed herein.

It will be understood that compounds of formula (I) may possess a chiral centre and may therefore exist as an isomer such as a racemate or an R- or S-enantiomer. The compounds may therefore be used as a purified enantiomer or diastereomer, or as a mixture of any ratio thereof. The isomers may be separated conventionally by chromatographic methods or using a resolving agent. Alternatively the individual isomers may be prepared by asymmetric synthesis using chiral intermediates. Where the compound has a carbon-carbon double bond, it may occur in Z- or E-form and all isomeric forms of the compounds being included in the present invention.

This invention also encompasses prodrugs of the compounds of formula (I).

The term "pro-drug" is used herein in its broadest sense to include those compounds which are converted in vivo to the compound of formula (I). Use of the prodrug strategy optimises the delivery of the drug to its site of action. In one embodiment, compounds of formula (I) having free amino, amido, hydroxyl, or carboxylic acid groups can be converted into prodrugs. Prodrugs include compounds wherein carbonates, carbamates, amide and alkyl esters which are covalently bonded to the above substituents of compounds of the present invention through a carbonyl carbon prodrug sidechain. Prodrugs may also include N-oxides of ring nitrogen atoms in formula (I).

Viral Polymerase Inhibition

The ability of the compounds of formula (I) to inhibit RNA synthesis by the RNA dependent RNA polymerase of HCV (NS5B) can be demonstrated by any assay capable of measuring RNA dependent RNA polymerase activity. A suitable assay is described in the examples.

While the invention is described with particular reference to compounds having inhibitory activity against a HCV NS5B polymerase, it will be understood that other polymerases can, if desired, be substituted in whole or in part for the HCV polymerase herein described. For example, one microbial polymerase target is HCV NS5B which is the viral RNA-dependent RNA polymerase (RdRp) that is responsible for viral replications. HCV NS5B protein, is released from a polyprotein and is involved in the synthesis of double-stranded RNA from a single-stranded viral RNA genome. It is believed that the replication and/or reproduction of HCV virus may be inhibited or prevented through the inhibition of NS5B and suppress or prevent the formation of the double-stranded HCV RNA.

To demonstrate that the compounds of formula (I) act by specific inhibition of NS5B, the compounds may be tested for the lack of inhibitory activity in an assay measuring the activity of an RNA-dependent RNA polymerase other than HCV polymerase or in a DNA dependent RNA polymerase assay.

Pharmaceutical Compositions

The invention also provides a pharmaceutical composition comprising a compound of formula (I) and a pharmaceutically acceptable carrier.

The pharmaceutical composition may further comprise or be administered in combination with one or more other antiviral agents such as Ribavirin (Copegus® or Rebetol®), an antiviral nucleoside inhibitor of NS5B polymerase (such as 4-amino-7-(2-C-methyl-β-D-ribofuranosyl)-pyrrolo[2,1-f][1,2,4]triazine; PSI-7977; PSI-938; RG7128 or mericitabine; IDX-184; INX-189 and other such agents that may be developed), a non-nucleoside inhibitor of NS5B polymerase (such as GS-9190 or tegobuvir; PF-868554 or filibuvir; VX-222; IDX-375; ABT-072; ABT-333; ANA-598 or setrobuvir; B1207127; JTK-853; GS-9669; and other such agents that may be developed), a NS3/4a protease inhibitor (such as telaprevir or Incivek®; boceprevir or Victrelis®; BI-201335; TMC-435; RG-7227 or danoprevir; MK-7009 or vaniprevir; GS-9451; GS-9256; BMS-650032; ACH-1625; ACH-2684; MK-5172; ABT-450; IDX-320; SCH-900518 and other such agents that may be developed), an NS5A inhibitor (such as BMS-790052 (daclatasvir); GS-5885; ABT-267; PPI-461; ACH-2928; GSK2336805 and other such agents that may be developed) and/or inhibitor of viral entry, assembly or egress. The composition may also additionally comprise at least one immunomodulatory agent for example an interferon or interferon derivative such as interferon alpha 2B (such as Intron® A interferon available from Schering Corp., Kenilworth, N.J.), pegylated interferon alpha 2A (such as Pegasys® available from Hoffmann-LaRoche, Nutley, N.J.), pegylated interferon alpha 2B (such as Peg-Intron® available from Schering Corp., Kenilworth, N.J.), consensus interferon (such as interferon alphacon-1, or Infergen® available from Valeant Pharmaceuticals, Costa Mesa, Calif.), interferon alpha 2A, recombinant interferon alpha 2A (such as Roferon® available from Hoffmann-LaRoche, Nutley, N.J.), or lymphoblastoid interferon tau, and/or an inhibitor of inosine-5'-monophosphate dehydrogenase (IMPDH) and other large or small molecules known to modulate host immune responses.

Accordingly, in one embodiment of the pharmaceutical composition, the other antiviral agent is Ribavarin optionally in combination with peg-IFN.

In another embodiment, the other antiviral agent is an NS5B inhibitor, more particularly a nucleoside inhibitor such as the bicyclic nucleosides and nucleotides of the general formula described in WO2010/002877, for example, 4-amino-7-(2-C'-methyl-3-D-ribofuranosyl)-pyrrolo[2,1-f][1,2,4]triazine.

In yet another embodiment, the other antiviral agent is an NS3/4A protease inhibitor such as telaprevir (VX-950) or Incivek®; boceprevir or Victrelis®; BI-201335; TMC-435; RG-7227 or danoprevir; MK-7009 or vaniprevir; GS-9451; GS-9256; BMS-650032; ACH-1625; ACH-2684; MK-5172; ABT-450; IDX-320; SCH-900518, particularly telaprevir (VX-950).

In still another embodiment, the other antiviral agent is an NS5A inhibitor such as BMS-790052 (daclatasvir); GS-5885; ABT-267; PPI-461; ACH-2928; GSK2336805, particularly BMS-790052 (daclatasvir).

It will be understood that combined administration of the compounds of the invention with the other antiviral agent may be concurrent, sequential or separate administration.

The term "composition" is intended to include the formulation of an active ingredient with conventional carriers and excipients, and also with encapsulating materials as the carrier, to give a capsule in which the active ingredient (with or without other carriers) is surrounded by the encapsulation carrier. Any carrier must be "pharmaceutically acceptable" meaning that it is compatible with the other ingredients of the composition and is not deleterious to a subject. The compositions of the present invention may contain other therapeutic agents as described above, and may be formulated, for example, by employing conventional solid or liquid vehicles or diluents, as well as pharmaceutical additives of a type appropriate to the mode of desired administration (for example, excipients, binders, preservatives, stabilizers, flavours, etc.) according to techniques such as those well known in the art of pharmaceutical formulation (See, for example, Remington: *The Science and Practice of Pharmacy*, 21st Ed., 2005, Lippincott Williams & Wilkins).

The pharmaceutical composition includes those suitable for oral, rectal, nasal, topical (including buccal and sublingual), vaginal or parenteral (including intramuscular, subcutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compositions according to the present invention may thus be formulated for parenteral administration (e. g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems for the compounds, and may contain, for example, water, ethanol, polyol (for example, glycerol, propylene glycol and liquid polyethylene glycol, and the like), suitable mixtures thereof, and vegetable oils.

Pharmaceutical forms suitable for injectable use may be delivered by any appropriate route including intravenous, intramuscular, intracerebral, intrathecal, epidural injection or infusion.

Sterile injectable solutions are prepared by incorporating the active compounds in the required amount in the appropriate solvent with various other ingredients such as these enumerated above, as required, followed by filtered sterilization. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile-filtered solution of the active ingredient plus any additional desired ingredients.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like.

The amount of active compound in therapeutically useful compositions should be sufficient that a suitable dosage will be obtained.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound (s) may be incorporated into sustained-release preparations and formulations, including those that allow specific delivery of the active peptide to specific regions of the gut.

Aqueous solutions suitable for oral use can be prepared by dissolving the active component in water and adding suitable colorants, flavours, stabilising and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Pharmaceutically acceptable carriers and/or diluents include any and all solvents, dispersion media, coatings, antibacterial and antifungal agents, isotonic and absorption delaying agents and the like.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP).

Conveniently the powder carrier will form a gel in the nasal cavity. The powder composition may be presented in unit dose form for example in capsules or cartridges of, e.g. gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the dosage unit forms are dictated by and directly dependent on (a) the unique characteristics of the active material and the particular therapeutic effect to be achieved, and (b) the limitations inherent in the art of compounding such an active material for the treatment of a HCV viral infection in living subjects having a diseased condition in which bodily health is impaired.

The invention also includes the compounds in the absence of carrier where the compounds are in unit dosage form.

Compositions comprising compounds of the invention formulated for oral delivery either alone or in combination with another HCV antiviral agent are particularly preferred.

As such, in one embodiment there is provided a pharmaceutical composition comprising a compound of formula (I) or salts, N-oxides, solvates, hydrates, racemates, enantiomers or diastereomers thereof, a pharmaceutically acceptable carrier and optionally another HCV antiviral agent selected from the group consisting of Ribavarin, an NS5B inhibitor, an NS3/4A protease inhibitor and an NS5A inhibitor. In a further embodiment the pharmaceutical composition may additionally comprising at least one immunomodulatory agent such as peg-IFN. In still a further particularly preferred embodiment, the pharmaceutical composition is administered in an effective amount to a subject in need of treatment for a HCV infection.

Methods of Treatment

The compounds of formula (I) may be used in the treatment of a Flaviviridae viral infection such as a HCV infection.

Generally, the term "treatment" means affecting a subject, tissue or cell to obtain a desired pharmacological and/or physiological effect and includes: (a) inhibiting the viral infection, i.e. arresting its development or further development; (b) relieving or ameliorating the effects of the viral infection, i.e. cause regression of the effects of the viral infection; (c) reducing the incidence or the viral infection or (d) preventing the infection from occurring in a subject, tissue or cell predisposed to the viral infection disease or at risk thereof, but has not yet been diagnosed with a protective pharmacological and/or physiological effect so that the viral infection does not develop or occur in the subject, tissue or cell.

The prevention of hepatitis C means, for example, administration of a pharmaceutical agent to a subject found to carry a HCV by a test and the like but without a symptom of infection, or to a subject who shows an improved disease state of hepatitis after a treatment of hepatitis C, but who still carries a HCV and is associated with a risk of recurrence of hepatitis.

The term "subject" as used herein refers to any animal, in particular mammals such as humans having a disease or condition which requires treatment with the compound of formula (I).

The term "administering" refers to providing the compound or pharmaceutical composition of the invention to a subject suffering from or at risk of the diseases or conditions to be treated or prevented.

The term "viral infection" refers to the introduction of a virus into cells or tissues, e.g., hepatitis C virus (HCV). In general, the introduction of a virus is also associated with replication. Viral infection may be determined by measuring virus antibody titer in samples of a biological fluid, such as blood, using, e.g., enzyme immunoassay. Other suitable diagnostic methods include molecular based techniques, such as RT-PCR, direct hybrid capture assay, nucleic acid sequence based amplification, and the like. A virus may infect an organ, e.g., liver, and cause disease, e.g., hepatitis, cirrhosis, chronic liver disease and hepatocellular carcinoma.

The term "Flaviviridae virus" refers to a virus of the family Flaviviridae, which family includes the Hepacivirus Flavivirus and Pestivirus or hepatitis C-like virus genera. A representative species of the genus of hepatitis C-like viruses is hepatitis C virus.

Dosages

The term "therapeutically effective amount" refers to the amount of the compound of formula (I) that will elicit the biological or medical response of a subject, tissue or cell that is being sought by the researcher, veterinarian, medical doctor or other clinician.

In the prevention or treatment of HCV infections or diseases an appropriate dosage level will generally be about 0.01 to 500 mg per kg subject body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. The dosage may be selected, for example to any dose within any of these ranges, for therapeutic efficacy and/or symptomatic adjustment of the dosage to the subject to be treated.

It will be understood that the specific dose level and frequency of dosage for any particular subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the subject undergoing therapy.

It will further be understood that when the compounds of the invention are to be administered in combination with one or more HCV antiviral agents the dosage forms and levels may be formulated for either concurrent, sequential or separate administration or a combination thereof.

General Method(s)

Compounds of the invention may be generally prepared by the following general method(s).

Compounds of formula (I) may be generally synthesized via a synthetic intermediate of general formula (II) as previously described. Suitable coupling conditions will be familiar to those skilled in the art and include, but are not limited to, alkylation and Mitsunobu, reactions.

It will be understood that unless otherwise defined each moiety having a substitutable hydrogen such as for example, alkyl, alkenyl, alkynyl, alkoxy, cycloalkyl, cycloalkenyl, heterocyclyl, aryl and heteroaryl, in each occurrence as described in the general schemes and methods which follow may be optionally substituted.

It will also be understood that the particular examples which are described herein may undergo further functionalisation using methods known in the art to form further examples of compounds of the invention.

General Method A

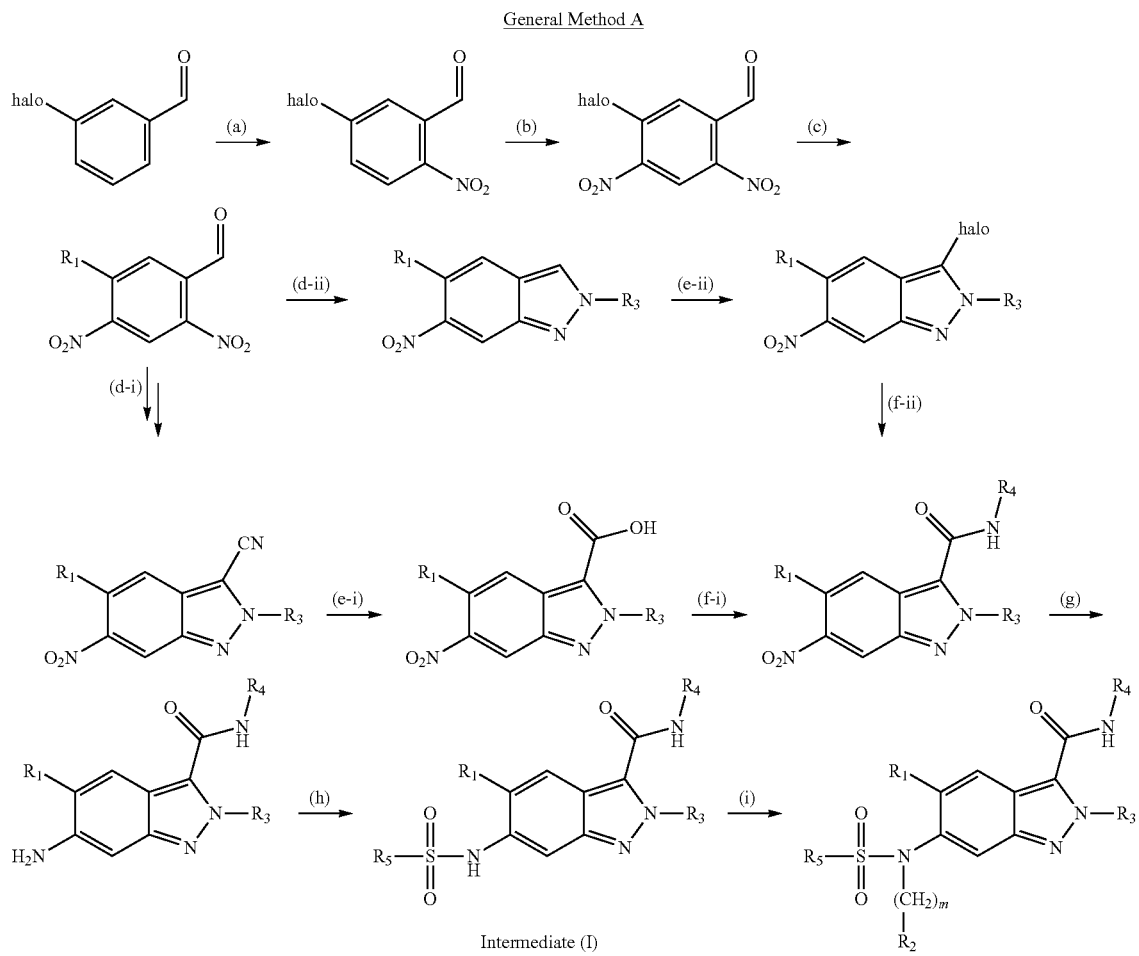

General Method A

Intermediate (I)

Formula (I)

Scheme 1:

where $R_1$ may be, for example, $C_3$-6cycloalkyl such as cyclopropyl, $C_{1-6}$alkyl including methyl, ethyl, n-propyl and iso-propyl, halo or $C_{1-6}$alkoxy including methoxy, ethoxy, n-propoxy and iso-propoxy; $R_3$ may be, for example, optionally substituted aryl or optionally substituted heteroaryl; $R_4$ may be, for example, H or $C_{1-6}$alkyl; $R_5$ may be, for example, $C_{1-6}$alkyl including methyl, ethyl, n-propyl and iso-propyl preferably methyl or $C_{1-3}$alkylhalo (i.e. $C_{1-3}$alkyl substituted with halo such as $CF_3$ or $CHF_2$) and $R_2$ is an optionally substituted 4-membered heterocyclic ring.

Synthesis of Intermediate (I)

Step a)

The arylaldehyde was nitrated using a mixture of fuming nitric acid and sulfuric acid to give a mixture of mono-, di- and tri-nitrated products.

Step b)

The mono-nitrohaloarylaldehyde was separated by conventional separation techniques (e.g. column chromatography) and again subjected to the nitrating conditions described above to give the corresponding dinitroarylhaloarylaldehyde.

Step c)

The dinitroarylhaoloaldehyde was reacted with a suitably substituted boronic acid or boronic acid derivative in the presence of a suitable catalyst (e.g. tetrakistriphenylphosphinepalladium(0)) and a suitable base (e.g. sodium carbonate) in a suitable solvent (e.g. toluene) as described by Miyaura and. Suzuki (see Miyaura, N.; Suzuki, A. *J. Chem. Soc., Chem. Commun.* 1979, 866-867) to give the corresponding dinitroaldehyde.

Step d-i)

The dinitroaldehyde was then reacted with a primary aryl- or alkylamine (e.g. 4-bromoaniline) in the presence of a cyanide source (e.g. sodium cyanide) and acetic acid and acetic anhydride to give the corresponding nitrocyanoindazole-N-oxide where $R_3$ is an optionally substituted aryl or heteroaryl moiety. The nitrocyanoindazole-N-oxide can be converted to the corresponding nitrocyanoindazole by treatment with a reagent such as phosphorus (III) trichloride.

Step e-i) The cyano group of the nitrocyanoindazole can then be hydrolysed to the corresponding nitroindazole carboxylic acid (e.g. using NaOH in aqueous EtOH)

Step f-i)

The nitroindazole carboxylic acid can then be coupled to an amine using standard peptide coupling conditions (e.g. HATU I/DIPEA/acetonitrile) to give the nitroindazole-amide.

Step d-ii)

Alternatively, the dinitroaldehyde is treated with a suitably substituted primary arylamine (e.g. phenyl amine) heteroarylamine (e.g. pyridin-2-amine such as 5-$C_{1-3}$alkyl-pyridin-2-amine or 5-halo-pyridin-2-amine) in a suitable solvent (e.g. EtOH) to give the corresponding imine, which is then treated in the same reaction with triphenylphosphine to give the corresponding nitroindazole.

Step e-ii)

The nitroindazole derived from step d-ii) was treated with a suitable halogenating reagent (e.g. N-bromosuccinimide) in a suitable solvent (e.g. DMF) to give the corresponding halonitroindazole.

Step f-ii)

The halonitroindazole derived from step e-ii) was dissolved in a suitable solvent (e.g. THF) and treated with a suitable primary amine (e.g. methylamine) in the presence of a suitable catalyst (e.g. tetrakis(triphenylphosphine)palladium(0) and carbon monoxide to give, on work-up, the corresponding nitroindazoleamide.

Step g)

The nitroindazoleamide can then be reduced to the corresponding nitroindazoleamine using standard conditions normally associated with the reduction of an arylnitro-group to an aniline (e.g iron in the presence of an aqueous alcoholic solvent).

Step h)

The amino analogue was first converted to the bis-sulfonyl analogue using standard sulfonylation conditions with an activated sulfonic acid (e.g. methanesulfonyl chloride) and base (e.g. DIPEA) in an organic solvent (e.g. DCM). The bis-sulfonyl analogue then underwent hydrolysis using base (e.g. potassium hydroxide) in aqueous alcoholic solvent (e.g. EtOH) to give the desired sulfonamide. Alternatively, the amino analogue was converted directly to the desired sulphonamide by reaction with the activated sulfonic acid (e.g. difluoromethanesulfonyl chloride) in a basic organic solvent (e.g pyridine).

Coupling Conditions

Step i)

The compounds of general formula (I) may then be generally prepared from Intermediate (I) i.e. compound of formula (II) as previously defined by: (i) coupling an optionally substituted alkyl-halo/triflate/tosylate/mesylate moiety under alkylation conditions i.e. the sulphonamide compound of formula (II) is dissolved/suspended in a suitable solvent (e.g. ACN) and treated with a suitable alkyl mesylate, triflate, tosylate or halide in the presence of a suitable base (e.g. potassium carbonate) to give, upon work-up, the corresponding alkylated sulphonamide of formula (I); or alternatively, (ii) coupling a hydroxylated precursor moiety under Mitsunobu reaction conditions wherein the sulphonamide compound of formula (II) and a suitably substituted primary or secondary alcohol in a suitable solvent (e.g. THF) is treated with triphenylphosphine and a suitable di-imide or di-imide equivalent (e.g. DIAD) to give, upon work-up, the corresponding substituted sulphonamide of formula (I).

It will be understood that the precursor moieties i.e. of general formula (III) as previously defined may contain an optionally substituted 4-membered heterocyclic ring or alternatively, the optionally substituted 4-membered heterocyclic ring may be introduced into a suitable precursor component e.g. a diol or alkene, of the compound by undergoing further functionalisation using methods known in the art.

EXAMPLES

Those skilled in the art will appreciate that the invention described herein is susceptible to variations and modifications other than those specifically described. The invention will now be described without limitation by reference to the non-limiting examples which follow.

Synthetic Methods $^1$H NMR spectra were recorded on either a Bruker Avance DRX 400, AC 200 or AM 300 spectrometer. Spectra were recorded in deuterated solvents (CDCl$_3$, MeOD, DMSO, CD$_3$CN, or Acetone) using the residual solvent peak as a reference. Chemical shifts are reported on the δ scale in parts per million (ppm) using the following conventions to assign the multiplicity: s (singlet), d (doublet), t (triplet), q (quartet), p (pentet), m (multiplet) and prefixed br (broad). Mass spectra (ESI) were recorded on either a Micromass Platform QMS or Thermo Finnigan LCQ Advantage spectrometer. Flash chromatography was performed on 40-63 μm silica gel 60 (Merck No. 9385). Automated flash chromatography was performed either on a Combi-Flash™ purification system using Combi-Flash™ silica gel columns or on a Biotage SP4 purification system using either GraceResolv™ silica gel cartridges, Grace Reveleris™ C-18 reverse phase silica gel cartridges or Biotage SNAP™ C-18 reverse phase silica gel cartridges. Preparative HPLC was carried out using either a Gilson 322 pump with a Gilson 215 liquid handler and a HP1100 PDA detector or an Agilent 1200 Series mass detected preparative LCMS using a Varian XRs C-18 100× 21.2 mm column. Unless otherwise specified, the HPLC systems employed Phenomenex C8(2) columns using either acetonitrile or acetonitrile containing 0.06% TFA in water, water containing 0.1% TFA or water containing 0.1% formic acid.

During the reactions a number of the moieties may need to be protected. Suitable protecting groups are well known in industry and have been described in many references such as Protecting Groups in Organic Synthesis, Greene T W, Wiley-Interscience, New York, 1981.

The abbreviations used in the Examples are as follows unless indicated otherwise:
Ac: acetyl
ACN: acetonitrile
aq.: aqueous
conc.: concentrated
CV: column volume
d. day
dba: dibenzylideneacetone
DCM: dichloromethane
DIPEA: N,N-diisopropylethylamine
DMF: N,N-dimethylformamide
DMSO: dimethylsulfoxide
dppf: 1,1'-bis(diphenylphosphino)ferrocene
EtOAc: ethyl Acetate
EtOH: ethanol
ESI: electrospray ionisation
h: hour(s)
HATU: 2-(7-Aza-1H-benzotriazole-1-yl)-1,1,3,3-tetramethyluronium hexafluorophosphate
HPLC: high performance liquid chromatography
LCMS: liquid chromatography coupled mass spectrometry
min: minute(s)
MeOH: methanol
MS: mass spectrometry
NBS: N-bromosuccinimide
NMR: nuclear magnetic resonance
PyBOP: benzotriazol-1-yl-oxytripyrrolidinophosphonium hexafluorophosphate
s: second(s)
SM: starting material
RT: room temperature
TEA: triethylamine
THF: tetrahydrofuran
TFA: trifluoroacetic acid
TLC: thin-layer chromatography Compounds of Formula (I)
Compound(s) of Formula (I) where $R_3$ is a Substituted Aryl (Phenyl) Group 2-(4-Chlorophenyl)-5-cyclopropyl-N-methyl-6-[(methylsulfonyl)amino]-2H-indazole-3-carboxamide (1)

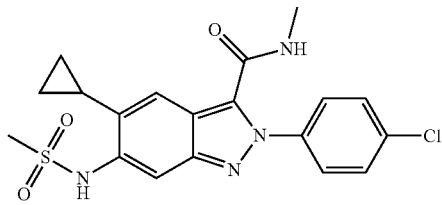 [SMILES: CNC(=O)c1c2cc(C3CC3)c(NS(C)(=O)=O)cc2nn1-c1ccc(Cl)cc1]

5-Bromo-2-nitrobenzaldehyde (ii)

To ice cold conc. sulphuric acid (400 mL) was added fuming nitric acid (200 mL) dropwise followed by 3-bromobenzaldehyde (i) (100 g, 0.540 mol) dropwise over 15 min. The reaction mixture was stirred for 10 min and then poured carefully over ice-water. The resulting solids were filtered and then purified by flash column chromatography on silica gel, eluting with EtOAc:n-hexane (gradient elution from 1% to 20% v/v) to give (ii) (60 g, 48%).

5-Bromo-2,4-dinitrobenzaldehyde (iii)

To ice cold conc. sulphuric acid (360 mL) was added fuming nitric acid (180 mL) dropwise followed by (ii) (60 g, 0.26 mol) dropwise over 15 min. The reaction mixture was stirred for 10 min and then allowed to warm to RT. After 30 min, the reaction mixture was heated at 45° C. for 2 h and then at 50° C. for 3 h and then allowed to cool to RT. The reaction mixture was then poured carefully over ice-water and the organics were extracted into chloroform (500 mL). The volatiles were dried (MgSO₄) and concentrated in vacuo. The residue was purified by flash column chromatography eluting with EtOAc:n-hexane (gradient elution from 5% to 30% v/v) to give (iii) (5.1 g, 7%).

5-Cyclopropyl-2,4-dinitrobenzaldehyde (iv)

To a stirred solution of (iii) (3 g, 10.9 mmol) in toluene (75 mL) was added a solution of sodium carbonate (2.29 g, 21.8 mmol) in water (15 mL). The mixture was sparged with nitrogen for 10 min whereupon cyclopropyl boronic acid (1.4 g, 16.4 mmol) and tetrakis(triphenylphosphine) palladium(0) (0.25 g, 0.22 mmol) were added and the reaction mixture was heated at reflux and progress monitored by TLC. After heating for 6 h the reaction was then cooled to RT and diluted with EtOAc (100 mL). The organic layer was separated and concentrated in vacuo. Purification of the residue by column chromatography on silica gel to gave (iv) (2 g, 78%).

2-(4-Chlorophenyl)-5-cyclopropyl-6-nitro-2H-indazole-3-carbonitrile (v)

To a stirred suspension of (iv) (20 g, 0.09 mol) in acetic acid (400 mL) was added 4-chloroaniline (21.6 g, 0.17 mol) and the reaction heated at 60° C. to obtain a complete solution. To this solution was added sodium cyanide (20 g, 0.41 mol) portionwise over 20 min. The reaction mixture was stirred for 5 min whereupon acetic anhydride (6 mL) was added. Upon the formation of a precipitate, an additional quantity of sodium cyanide (20 g, 0.41 mol) was added portionwise. After stirring for 1 h, the reaction mixture was cooled to RT, diluted with MeOH (30 ml) and the solids separated by filtration. The solid cake was dissolved in chloroform (400 ml) and the organics washed with water (2×100 ml), dried (MgSO$_4$) and concentrated in vacuo to give the intermediate 2-(4-chlorophenyl)-5-cyclopropyl-6-nitro-2H-indazole-3-carbonitrile 1-oxide (34.6 g). ESI-MS m/z calculated for [M+H]$^+$: 355.1. found: 355.2. $^1$H NMR (400 MHz, CDCl$_3$) δ 8.32 (s, 1H), 7.72-7.50 (m, 5H), 2.44-2.30 (m, 1H), 1.18-1.05 (m, 2H), 0.85-0.71 (m, 2H).

To a stirred solution of the crude intermediate 2-(4-chlorophenyl)-5-cyclopropyl-6-nitro-2H-indazole-3-carbonitrile 1-oxide (23 g, 0.06 mmol) in chloroform (230 mL) was added phosphorus trichloride (23 mL) and the reaction mixture was then heated at 60° C. After 2 h, the reaction was cooled to RT and ice-water added (ca. 200 mL). The organics were extracted into DCM (3×200 mL), dried (Na$_2$SO$_4$) and concentrated in vacuo to give (v) (20.3 g, 92%), which was used unpurified in subsequent steps. ESI-MS m/z calculated for [M+H]$^+$: 339.1. found: 339.0. $^1$H NMR (400 MHz, CDCl$_3$) δ 8.25 (s, 1H), 7.92-7.81 (m, 2H), 7.69-7.57 (m, 3H), 2.42-2.29 (m, 1H), 1.14-1.03 (m, 2H), 0.82-0.72 (m, 2H).

2-(4-Chlorophenyl)-5-cyclopropyl-6-nitro-2H-indazole-3-carboxylic acid (vi)

To a stirred solution of (v) (20 g, 0.06 mol) in EtOH:water (400 ml, 1:1 v/v) was added NaOH (59.0 g, 0.02 mol) and the reaction mixture heated at 90° C. for 15 h. The reaction was then cooled to RT and the volatiles were removed in vacuo. The residual aqueous solution was acidified to pH 2 with aq. 2N HCl solution whereupon a solid precipitated from solution. The solid was separated by filtration and dissolved in EtOAc (300 mL), dried (Na$_2$SO$_4$) and concentrated in vacuo to give (vi) (7.5 g, with purity 75% by HPLC analysis). The material was used unpurified in subsequent steps.

ESI-MS m/z calculated for [M+H]$^+$: 358.0. found: 358.0. $^1$H NMR (400 MHz, d$_6$-DMSO) δ 8.22 (s, 1H), 7.93 (s, 1H), 7.76-7.52 (m, 2H), 7.29-7.09 (m, 2H), 2.39-2.19 (m, 1H), 1.05-0.93 (m, 2H), 0.73-0.65 (m, 2H).

2-(4-Chlorophenyl)-5-cyclopropyl-N-methyl-6-nitro-2H-indazole-3-carboxamide (vii)

To a stirred solution of (vi) (15 g, unpurified from the previous step) in DMF (300 mL) was added DIPEA (27.7 mL, 0.16 mol), HATU (23.9 g, 0.06 mol) and methylamine (2.0M solution in THF, 60 mL, 0.12 mol). The reaction mixture was stirred for 2 h at RT and then poured onto the ice. The precipitate was then separated by filtration and solid obtained was dissolved in DCM (300 mL), dried (Na$_2$SO$_4$) and the volatiles removed in vacuo to give (vii) (16.5 g with purity 86.5% by HPLC analysis), which was used unpurified in subsequent steps. ESI-MS m/z calculated for [M+H]$^+$: 371.1. found: 371.0. $^1$H NMR (400 MHz, CDCl$_3$) δ 8.23 (s, 1H), 7.74 (s, 1H), 7.62-7.45 (m, 4H), 5.91 (brs, 1H), 3.09-2.97 (m, 3H), 2.40-2.28 (m, 1H), 1.04-0.95 (m, 2H), 0.73-0.65 (m, 2H).

6-Amino-2-(4-chlorophenyl)-5-cyclopropyl-N-methyl-2H-indazole-3-carboxamide (viii)

To a solution of (vii) (127 mg, 0.34 mmol) in THF (2.5 mL) and MeOH (7.5 mL) was added Raney nickel (20 mg) and the reaction stirred vigorously under hydrogen atmosphere at 60° C. for 2 h. The reaction was diluted with MeOH (40 mL), filtered and then concentrated to dryness to give (viii) (97 mg, 83%). ESI-MS m/z calculated for [M+H]$^+$: 341.1. found: 341.0. $^1$H NMR (400 MHz, d$_6$-DMSO) δ 7.58-7.47 (m, 4H), 7.23 (s, 1H), 6.64 (m, 1H), 2.85-2.76 (m, 3H), 1.82-1.72 (m, 1H), 0.96-0.89 (m, 2H), 0.64-0.55 (m, 2H).

2-(4-Chlorophenyl)-5-cyclopropyl-N-methyl-6-[(methylsulfonyl)amino]-2H-indazole-3-carboxamide (1)

To a stirred solution of (viii) (3.0 g, 8.8 mmol) in DCM (90 ml) was added DIPEA (5.4 mL, 30.8 mmol.) and the reaction mixture cooled to 0° C. Methanesulfonyl chloride (1.70 mL, 22.0 mmol) was added dropwise and the reaction stirred for 2 h. Water (100 mL) was then added to the reaction and pH of the aqueous layer adjusted to pH~5 using aq. 2N HCl. The organics were separated and the aqueous layer was extracted into EtOAc (2×100 mL). The combined organics were dried (Na$_2$SO$_4$) and concentrated in vacuo. A portion of the solid obtained (2.6 g) was dissolved in EtOH (166 mL), solid potassium hydroxide (2.82 g, 50.3 mmol) was added and the reaction heated at 50° C. After 2 h, the reaction mixture was cooled to RT, diluted with water (100 mL) and the pH adjusted to 5 using aq. 2N HCl. The organics were extracted into EtOAc (3×100 mL), dried (Na$_2$SO$_4$) and concentrated in vacuo to give 4 g crude of the desired product. A portion of the crude material (1 g) was purified by column chromatography on silica gel eluting with EtOAc:n-hexane (gradient elution from 10% to 40% v/v) to give Compound (1) (330 mg). ESI-MS m/z calculated for [M+H]$^+$: 419.1. found: 419.1. $^1$H NMR (400 MHz, d$_6$-Acetone) δ 7.79 (brs, 1H), 7.66 (s, 1H), 7.61 (brs, 1H), 7.56-7.51 (m, 2H), 7.49 (s, 1H), 7.46-7.41 (m, 2H), 3.02 (s, 3H), 2.81 (d, J=4.7 Hz, 3H), 2.11-2.01 (m, 1H), 0.96-0.90 (m, 2H), 0.66-0.59 (m, 2H).

Compound(s) of Formula (II) where R$_3$ is a Substituted Heteroaryl (Preferably 6-Membered and Containing at Least One Nitrogen Atom) Group

5-Cyclopropyl-N-methyl-2-(5-methylpyridin-2-yl)-6-[(methylsulfonyl)amino]-2H-indazole-3-carboxamide (2)

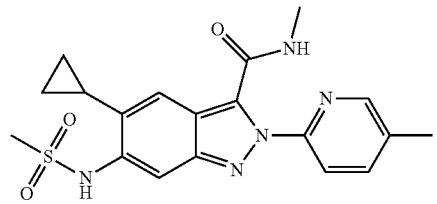

5-Cyclopropyl-2-(5-methylpyridin-2-yl)-6-nitro-2H-indazole (ii)

To a stirred solution of 5-cyclopropyl-2,4-dinitrobenzaldehyde (prepared according to the synthesis of Compound (1)) (50 mg, 0.212 mmol) in EtOH (750 mL) was added 5-methylpyridin-2-amine (25 mg, 0.23 mmol) and the resultant solution stirred at RT for 2d after which time a solid had precipitated from solution. Triphenylphosphine (167 mg, 0.64 mmol) was added in a single portion and the reaction then heated at 100° C. in a sealed tube for 4 h. Upon cooling to RT, the reaction was diluted with DCM (2 mL) and the organics were washed with aq. 30% hydrogen peroxide solution (2 mL). The organics were separated and filtered through a plug of MgSO$_4$ and then purified by automated column chromatography (Biotage SP4, Grace 4 g silica cartridge) eluting with EtOAc:n-heptane (gradient elution, 0% equil. (2 CV), 0% (1CV), 0 to 100% (35 CV), 100% (5 CV)) to give (ii) (27 mg, 43%). ESI-MS: calculated [M+H]$^+$ 295.1. observed [M+H]$^+$ 295.2.

3-Bromo-5-cyclopropyl-2-(5-methylpyridin-2-yl)-6-nitro-2H-indazole (iii)

To a solution of (ii) (1.08 g, 3.67 mmol) in DMF (15 mL) was added N-bromosuccinimide (780 mg, 4.40 mmol) and the resulting mixture stirred at 80° C. for 1.5 h. The reaction mixture was then cooled to RT and the solvent was removed under reduced pressure. The residue was dissolved in EtOAc (100 mL) and washed with aq. saturated sodium bicarbonate (20 mL) and brine (20 mL). The organic phase was dried (MgSO$_4$) and the volatiles removed in vacuo to give (iii) (1.37 g, >99%). ESI-MS: calculated [M+H]$^+$ 373.01375.0. observed [M+H]$^+$ 373.1/375.1.

5-Cyclopropyl-N-methyl-2-(5-methylpyridin-2-yl)-6-nitro-2H-indazole-3-carboxamide (iv)

Compound (iii) (5.80 g, 16.0 mmol), methylamine (2M solution in THF, 120 mL, 230 mmol) and tetrakis(triphenylphosphine)palladium(0) (2.00 g, 1.73 mmol) were placed in a medium pressure reaction vessel. The mixture was degassed and purged with carbon monoxide gas several times and then stirred at 70° C. under 40 psi of CO(g) for 1.5 hr. After cooling to RT, the resulting suspension was filtered and washed with EtOAc. The solid was set aside and the filtrate was concentrated under reduced pressure. The residue was triturated with EtOAc and the solids separated by filtration. The combined solids were dried in vacuo to give (iv) (6.00 g, >100%), which was used in subsequent steps without purification. ESI-MS: calculated [M+H]$^+$ 352.1. observed [M+H]$^+$ 352.1.

6-Amino-5-cyclopropyl-N-methyl-2-(5-methylpyridin-2-yl)-2H-indazole-3-carboxamide (v)

To a suspension of (iv) (5.6 g, 16.0 mmol) in EtOH (150 mL) and water (30 mL) was added ammonium chloride (6.25 g, 112.8 mmol) followed by iron powder (6.00 g, 112 mmol). The mixture was heated to 80° C. and stirred for 1.5 h whereupon the reaction mixture was filtered through celite, washed with MeOH (50 mL) and the combined filtrate then concentrated in vacuo. The residue was suspended in water and the solid separated by filtration. The residual solid was dried in vacuo at 50° C. for 12 h to give (v) (2.75 g, 53% over 2 steps from (iii)). ESI-MS: calculated [M+H]$^+$ 322.2 observed [M+H]$^+$ 322.2.

5-Cyclopropyl-N-methyl-2-(5-methylpyridin-2-yl)-6-[(methylsulfonyl)amino]-2H-indazole-3-carboxamide (2)

To a suspension of (v) (2.75 g, 8.6 mmol) in DCM (30 mL) at 0° C. was added DIPEA (4.40 mL, 25.0 mmol) followed by methanesulfonyl chloride (3.30 mL, 42.0 mmol). The reaction mixture was stirred at RT for 1 h and then washed with aq. sat'd. NaHCO$_3$ (50 mL), brine (50 mL) and dried (MgSO$_4$). Removal of solvent in vacuo gave the crude product, which was then dissolved in EtOH (100 mL) and 1,4-dioxane (20 mL). To the resultant solution was added KOH (~10 eq) portionwise at RT until the pH 8-9 was achieved. The reaction mixture was then slowly neutralised by addition of 1M HCl (aq) and volatiles removed in vacuo. The residue was taken up in EtOAc (50 mL) and washed with water (50 mL). The organic phase was dried (MgSO$_4$), concentrated in vacuo and the solid residue then triturated with EtOAc. The solid was separated by filtration and dried in a stream of air and purified further by automated column chromatography (Biotage SP4, 12 g Grace Resolve cartridge) eluting with EtOAc:n-heptane (gradient elution from 60% to 100%. v/v) to give Compound (2) (2.42 g, 72%). ESI-MS: calculated [M+H]$^+$ 400.1 observed [M+H]$^+$ 400.1. $^1$H NMR (400 MHz, CDCl$_3$) δ 8.94 (brd, J=3.9 Hz, 1H), 8.38 (s, 1H), 7.99 (s, 1H), 7.90 (d, J=8.3 Hz, 1H), 7.86-7.77 (m, 2H), 7.17 (s, 1H), 3.18 (s, 3H), 3.09 (d, J=4.7 Hz, 3H), 2.50 (s, 3H), 1.84-1.76 (m, 1H), 1.15-1.04 (m, 2H), 0.84-0.74 (m, 2H).

Compounds of Formula (III) for Coupling to Compounds of Formula (II)

An extensive selection of suitable compounds of formula (III) for coupling to compounds of formula (II) under suitable conditions, particularly alkylation and Mitsunobu conditions, are available from commercial suppliers or will be familiar to those in the art. A further diversity of compounds of formula (III) however may be prepared according to one or more of the following methods.

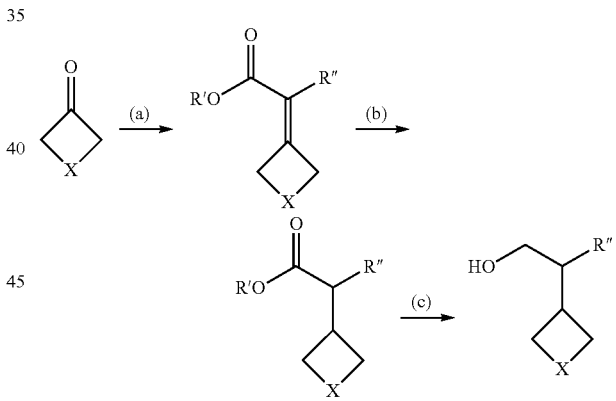

Scheme 2: Where X is O or NR where R is H or an Optional Substituent, R' is Alkyl and R" is an Optional Substituent.

Step a)

A suitably substituted alkylphosphonate is treated with a suitable base (e.g. potassium tert-butoxide) in a suitable solvent (e.g. THF) to give the corresponding phosphonium ylide. A substituted cyclic ketone can be added to the resultant ylide to form, on work-up, the corresponding α,β-unsaturated ester.

Step b)

The α,β-unsaturated ester derived from step a) can be reduced to the corresponding alkyl ester using standard hydrogenation conditions such as hydrogen gas in the presence of a suitable catalyst (e.g. 10% palladium on carbon) and a suitable solvent (e.g. ethanol).

Step c)

The ester derived from step b) can be reduced to the corresponding alcohol using a suitable reducing agent (e.g. lithium borohydride) in a suitable solvent (e.g. diethyl ether).

2-(oxetan-3-yl)propan-1-ol

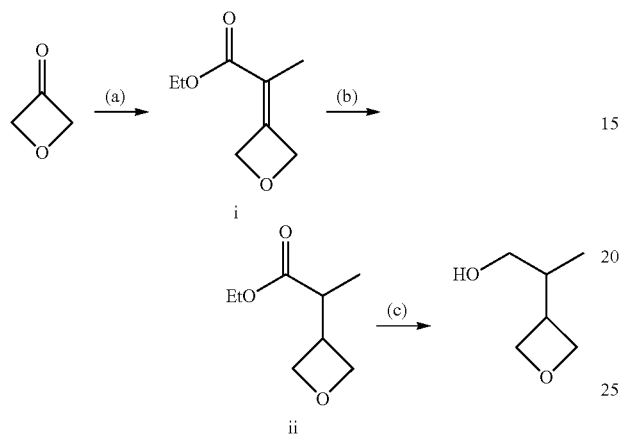

Ethyl 2-(oxetan-3-ylidene)propanoate (i)

To a solution of triethyl 2-phosphonopropionate (800 mg, 3.4 mmol) in anhydrous THF (3 mL) was added potassium tert-butoxide (340 mg, 3.1 mmol). The reaction was stirred for 1 h at RT then oxetan-3-one (CAS-RN 6704-31-0, available from commercial suppliers, 220 mg, 3.1 mmol) was added in a single portion. The reaction was heated at reflux for 20 h then cooled to RT and adsorbed onto silica gel. Purification by automated column chromatography (Biotage SP4) on silica gel (12 g Grace cartridges) eluting with EtOAc: n-heptane (gradient elution, 0% (equil., 5 CV), 0% (5 CV) 0-100% (25CV), 100% (10 CV)) afforded (i) (151 mg, 31%).

$^1$H NMR (400 MHz, CDCl$_3$) δ 5.44-5.37 (m, 2H), 5.30-5.23 (m, 2H), 4.17 (q, J=7.2 Hz, 2H), 1.68 (quint, J=1.8 Hz, 3H), 1.27 (t, J=7.2 Hz, 3H).

Ethyl 2-(oxetan-3-yl)propanoate (ii)

To a solution of (i) (151 mg, 0.97 mmol) in EtOH (54 mL) was added 10% Pd/C (50 mg, 0.05 mmol). The reaction was degassed and purged with hydrogen at balloon pressure (×3) then stirred under hydrogen at RT for 16 h. The reaction mixture was filtered and the residue washed with acetonitrile (10 mL). The combined organics were concentrated in vacuo and the residue, (ii) (148 mg), was used without further purification.

2-(Oxetan-3-yl)propan-1-ol: To a suspension of lithium borohydride (40 mg, 1.87 mmol) in anhydrous Et$_2$O (2.5 mL) at 0° C. was added to a solution of crude (ii) (148 mg, 0.94 mmol) in anhydrous Et$_2$O (2.5 mL). The reaction was warmed to RT and stirred for 18 h. Water (15 mL) was added cautiously to quench the reaction and the organics were extracted into EtOAc (3×15 mL), dried (MgSO$_4$) and concentrated in vacuo (without heating) to give 2-(oxetan-3-yl)propan-1-ol (105 mg, 97%). $^1$H NMR (400 MHz, CDCl$_3$) δ 4.80-4.70 (m, 2H), 4.55 (dt, J=20.0 and 6.4 Hz, 2H), 3.46 (brt, J=4.6 Hz, 2H), 2.98-2.84 (m, 1H), 2.14-2.00 (m, 1H), 0.87 (d, J=6.8 Hz, 3H).

Compounds of Formula (I)

Alkylation of Compounds of Formula (I) to Obtain Compounds of Formula (I)

5-Cyclopropyl-N-methyl-2-(4-methylphenyl)-6-{(methylsulfonyl)[2-(oxetan-3-yl)ethyl]amino}-2H-indazole-3-carboxamide (3)

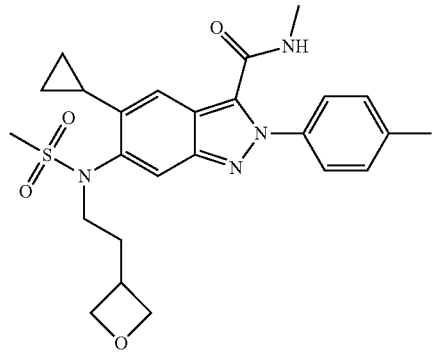

To a stirred solution of 2-(oxetan-3-yl)ethyl methanesulfonate (11 mg, 0.06 mmol, prepared by treating 2-(oxetan-3-yl)ethanol with methanesulfonyl chloride in DCM in the presence of DIPEA) was added 5-cyclopropyl-6-(methanesulfonamido)-N-methyl-2-(p-tolyl)indazole-3-carboxamide (24 mg, 0.06 mmol) followed by potassium carbonate (68 mg, 0.49 mmol). The resultant suspension was heated at 60° C. for 18 h whereupon another portion of (oxetan-3-yl)ethyl methanesulfonate (81 mg, 0.45 mmol) in ACN (2 mL) was added and heating/stirring continued. After 24 h, the reaction mixture was diluted with EtOAc (15 mL) and the organics washed with water (20 mL). The aqueous layer was back-extracted into EtOAc (15 mL) and the combined organics were then washed with brine (10 mL), dried (MgSO$_4$) and the volatiles removed in vacuo. The residue was purified by preparative HPLC eluting with ACN:0.1% formic acid in water (gradient elution, 5% to 30% to 40% to 100%) to give Compound (3) (4 mg, 14%). ESI-MS m/z calculated for [M+H]$^+$: 483.2 found: 483.1. $^1$H NMR (400 MHz, CD$_3$CN) δ 7.78 (s, 1H), 7.58 (s, 1H), 7.51 (d, J=8.2 Hz, 2H), 7.40 (d, J=7.94 Hz, 2H), 5.63 (brs, 1H), 4.86-4.78 (m, 2H), 4.40-4.33 (m, 2H), 3.70 (t, J=7.94 Hz, 2H), 3.18-3.05 (m, 4H), 2.98 (d, J=5.0 Hz, 3H), 2.51 (s, 3H), 2.47-2.38 (m, 1H), 2.17-1.97 (m, 2H), 1.19-1.03 (m, 3H), 0.72-0.63 (m, 1H).

Alkylation with Post-Coupling Ring Formation

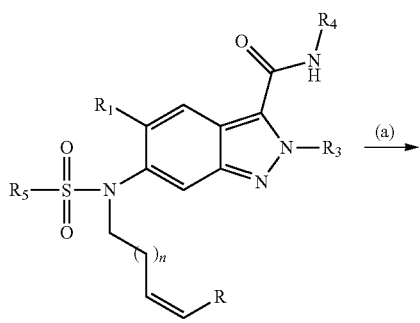

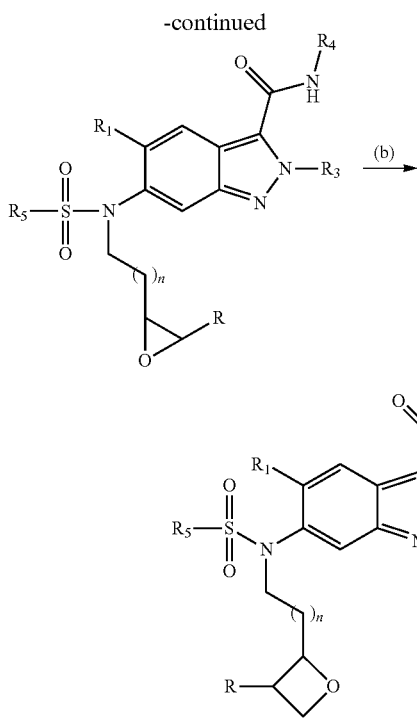

Scheme 3: Where R is an Optional Substituent as Previously Defined n is an Integer 0, 1, 2, 3, 4 or 5 and Each $(CH_2)_n$ Moiety when Present May be Independently Optionally Substituted with One or Two Substituents.

Step a)

The alkene was converted to the corresponding epoxide using standard epoxidation conditions (e.g. treatment with N-bromosuccinimide followed by aq. NaOH) in a suitable solvent(s) (e.g. 1,4-dioxane and acetic acid). The resultant epoxide can be isolated and purified or used crude in subsequent procedures.

Step b)

Trimethylsulfoxonium iodide dissolved in a suitable solvent (e.g. tert-butanol) and treated with a suitable base (e.g. potassium tert-butoxide). To the resultant ylide was added the epoxide derived from step a) to give the resultant substituted oxetane.

2-(4-Chlorophenyl)-5-cyclopropyl-N-methyl-6-{(methylsulfonyl)[3-(oxetan-2-yl)propyl]amino}-2H-indazole-3-carboxamide (4)

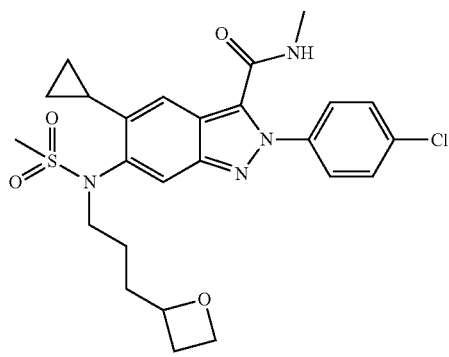 [SMILES: CNC(=O)c1c2cc(C3CC3)c(N(CCCC3CCO3)S(C)(=O)=O)cc2nn1-c1ccc(Cl)cc1]

2-(4-Chlorophenyl)-5-cyclopropyl-N-methyl-6-[(methylsulfonyl) (pent-4-en-1-yl)amino]-2H-indazole-3-carboxamide (i)

Synthesized under alkylation conditions by reacting 2-(4-chlorophenyl)-5-cyclopropyl-N-methyl-6-[(methylsulfonyl)amino]-2H-indazole-3-carboxamide (200 mg, 0.48 mmol) with 4-penten-1-ol (0.1 mL). Work up and purification afforded (i) (161 mg, 69%). $^1$H NMR (400 MHz, CDCl$_3$) δ 7.72 (d, J=0.5 Hz, 1H), 7.56-7.48 (m, 4H), 7.37 (s, 1H), 5.88-5.66 (m, 2H), 5.03-4.93 (m, 2H), 3.73 (t, J=7.8 Hz, 2H), 3.05 (s, 3H), 3.01 (d, J=4.9 Hz, 3H), 2.49-2.37 (m, 1H), 2.15-2.05 (m, 2H), 1.85-1.62 (m, 2H), 1.15-1.04 (m, 2H), 1.04-0.93 (m, 1H), 0.67-0.52 (m, 1H). ESI-MS m/z calculated for [M+H]$^+$: 487.2. found: 487.1.

2-(4-chlorophenyl)-5-cyclopropyl-N-methyl-6-{(methylsulfonyl)[3-(oxiran-2-yl)propyl]amino}-2H-indazole-3-carboxamide (ii)

To a solution of (i) (156 mg, 0.32 mmol) and acetic acid (37 μL, 0.64 mmol) in anhydrous 1,4-dioxane (15 mL) and water (20 mL) at 0° C. was added NBS (68 mg, 0.13 mmol) in a single portion. The reaction mixture was allowed to warm slowly to room temperature over 1 h 25 min whereupon aq. 1M NaOH solution (3 mL) was added and the reaction followed LCMS analysis. After 30 min, the reaction mixture was diluted with water (10 mL), extracted with EtOAc (3×10 mL) and the combined organics then dried (MgSO$_4$) and concentrated in vacuo to obtain (ii) (191 mg, >100%). The crude product was used without further purification in the next step. ESI-MS m/z calculated for [M+H]$^+$: 503.2. found: 503.1.

2-(4-chlorophenyl)-5-cyclopropyl-N-methyl-6-{(methylsulfonyl)[3-(oxetan-2-yl)propyl]amino}-2H-indazole-3-carboxamide (iii)

An oven-dried flask was charged with a mixture of potassium tert-butoxide (426 mg, 3.8 mmol) and trimethylsulfoxonium iodide (860 mg, 3.9 mmol) in anhydrous tert-butanol (7.5 mL) under argon. The reaction mixture was stirred vigorously at 50° C. for 5 h under argon then added to a stirred solution of crude (ii) (191 mg) in anhydrous tert-butanol (2.5 mL) in a single portion. The reaction was stirred at 50° C. overnight under argon, cooled to RT and concentrated in vacuo. The residue was then partitioned between water (50 mL) and EtOAc (50 mL) and the organics separated. The aqueous layer was extracted aq with EtOAc (2×50 mL) and the combined organic layers dried (MgSO$_4$) and concentrated in vacuo. The residue was dissolved in DMSO (2.5 mL) and the mixture centrifuged. The supernatant solution was collected and subjected to preparative HPLC (0.1% formic acid in acetonitrile: 0.1% formic acid in water, gradient elution 0% to 45% to 60% to 100%) to give Compound (4) (31 mg, 16% over 2 steps). $^1$H NMR (400 MHz, CD$_3$CN) δ 7.80 (s, 1H), 7.60-7.50 (m, 4H), 7.35 (s, 1H), 6.98 (br s, 1H), 4.75-4.64 (m, 1H), 4.55-4.46 (m, 1H), 4.39-4.31 (m, 1H), 3.78-3.69 (m, 2H), 3.07 (s, 3H), 2.89 (d, J=4.8 Hz, 3H), 2.64-2.53 (m, 1H), 2.42-2.32 (m, 1H), 2.31-2.19 (m, 1H), 1.81-1.49 (m, 3H), 1.09-0.97 (m, 3H), 0.67-0.58 (m, 1H). ESI-MS m/z calculated for [M+H]$^+$: 517.2. found: 517.0; m/z calculated for [M+Na]$^+$: 539.2. found: 539.1.

Mitsunobu Coupling of Compounds of Formula (II) and (III) to Obtain Compounds of Formula (I)

5-Cyclopropyl-N-methyl-2-(5-methylpyridin-2-yl)-6-{(methylsulfonyl)[2-(oxetan-3-yl)ethyl]amino}-2H-indazole-3-carboxamide (5)

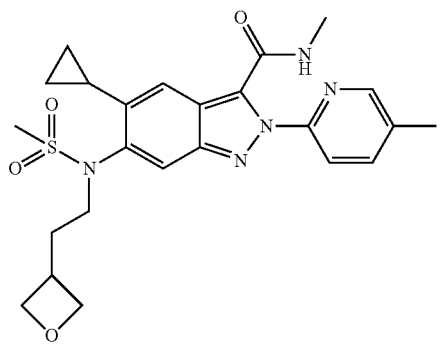

To a stirred suspension of 5-cyclopropyl-N-methyl-2-(5-methylpyridin-2-yl)-6-[(methylsulfonyl)amino]-2H-indazole-3-carboxamide (i) (11 mg, 0.03 mmol) and 2-(oxetan-3-yl)ethanol (5.6 mg, 0.06 mmol) in THF (200 μL) was added triphenylphosphine (11 mg, 0.04 mmol) followed by DIAD (8 μL, 0.04 mmol). The suspension dissolved slowly upon stirring. LCMS analysis of the reaction after 2.5 hr showed the presence of starting material and further aliquots of triphenylphosphine (5.0 mg, 0.05 mmol) and DIAD (8 μL, 0.04 mmol) were added. After stirring for 2 h, the reaction was diluted with EtOAc (10 mL), the organics washed with water (10 mL), brine (10 mL) and dried (MgSO$_4$). The organics were concentrated in vacuo and the residue purified by automated column chromatography on silica gel (Biotage SP4, 4 g Grace Resolve cartridge) eluting with acetic acid: DCM (10% v/v, 10 CV) to remove the triphenylphosphine oxide followed by MeOH: DCM (gradient elution, 0% to 20%, 20 CV) to give Compound (5) (7.8 mg, 59%). ESI-MS m/z calculated for [M+H]$^+$: 484.2. found: 484.2. $^1$H NMR (400 MHz, CDCl$_3$) δ 8.47 (brs, 1H), 8.36 (s, 1H), 7.83-7.76 (m, 2H), 7.72 (s, 1H), 7.60 (s, 1H), 4.84-4.71 (m, 2H), 4.34 (q, J=6.0 Hz, 2H), 3.74-3.56 (m, 2H), 3.10-2.99 (m, 7H), 2.47 (s, 3H), 2.30 (ddd, J=13.6, 8.3, 5.4 Hz, 1H), 2.07-1.95 (m, 2H), 1.09-0.94 (m, 3H), 0.65-0.56 (m, 1H).

Mitsunobu with Post-Coupling Substitution and/or Functionalization

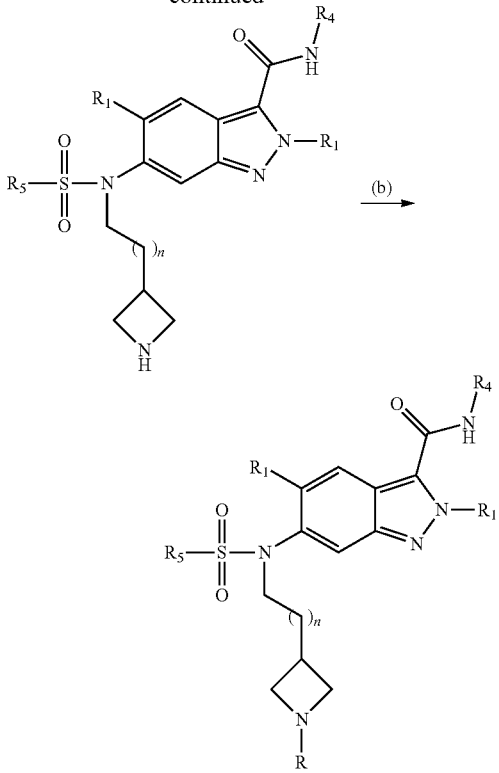

Scheme 4: Where R is a Substituent as Previously Defined and PG is a Suitable N-Protecting Group e.g. Tert-Butoxycarbonyl, n is an Integer 0, 1, 2, 3, 4 or 5 and Each (CH$_2$)$_n$ Moiety when Present May be Independently Optionally Substituted with One or Two Substituents.

Step a)
The protected azetidine is converted to the corresponding deprotected azetidine using standard conditions (for a list of protecting groups and conditions for their removal, see Greene, T. W., Wiley-Interscience, New York, 1981).

Step)
The azetidine derived from step a) is then dissolved in a suitable solvent (e.g. MeOH) and treated with an alkyl/aryl aldehyde or ketone (e.g. paraformaldehyde) in the presence of a reducing agent (e.g. sodium borohydride) to give, upon work-up, the corresponding alkylated azetidine. Alternatively, the azetidine from step a) can be N-alkylated with a suitably substituted alkyl halide, alkyl mesylate, alkyl tosylate or alkyl triflate using the alkylation conditions previously described.

6-{[2-(Azetidin-3-yl)ethyl](methylsulfonyl)amino}-2-(4-chlorophenyl)-5-cyclopropyl-N-methyl-2H-indazole-3-carboxamide (6)

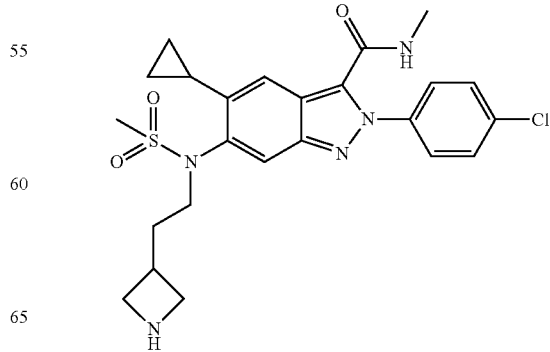

To a solution of tert-butyl 3-(2-{[2-(4-chlorophenyl)-5-cyclopropyl-3-(methylcarbamoyl)-2H-indazol-6-yl](methylsulfonyl)amino}ethyl)azetidine-1-carboxylate (prepared by reacting 2-(4-chlorophenyl)-5-cyclopropyl-N-methyl-6-[(methylsulfonyl)amino]-2H-indazole-3-carboxamide with tert-butyl 3-(2-hydroxyethyl)azetidine-1-carboxylate), (25 mg, 0.04 mmol) in DCM (3 mL) was added TFA (1 mL) and the reaction stirred at ambient temperature. After 1 h, the reaction was concentrated in vacuo and the residue partitioned between EtOAc (25 mL) and aq. saturated sodium bicarbonate (15 mL). The organic layer was separated and the aqueous layer extracted with EtOAc (3×15 mL). The combined organics were washed with brine (15 mL), dried (MgSO$_4$), concentrated in vacuo and purified by preparative HPLC eluting with acetonitrile:0.1% formic acid in water to afford Compound (6) (8.8 mg, 42%). ESI-MS m/z calculated for [M+H]$^+$: 502.2. found: 502.1 $^1$H NMR (400 MHz, CD$_3$CN) δ 8.40 (s, 1H), 7.83 (s, 1H), 7.64-7.54 (m, 4H), 7.39 (s, 1H), 7.37 (br d, J=3.9 Hz, 1H), 3.94-3.81 (m, 2H), 3.76-3.59 (m, 2H), 3.59-3.50 (m, 2H), 3.09 (d, J=10.3 Hz, 3H), 2.97-2.86 (m, 4H), 2.43-2.33 (m, 1H), 1.95-1.86 (m, 2H), 1.14-1.00 (m, 3H), 0.71-0.59 (m, 1H).

Post-Coupling Functionalisation (N-Alkylation by Reductive Amination)

2-(4-chlorophenyl)-5-cyclopropyl-N-methyl-6-{[2-(1-methylazetidin-3-yl)ethyl](methylsulfonyl)amino}-2H-indazole-3-carboxamide (7)

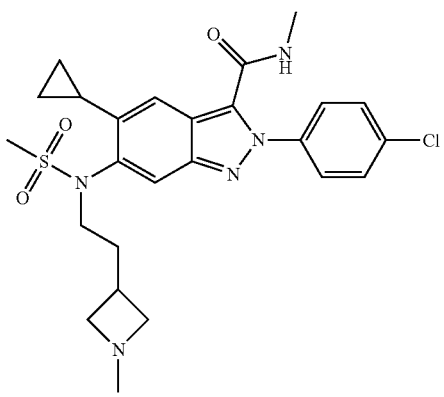 [SMILES: CNC(=O)c1c2cc(C3CC3)c(N(CCC3CN(C)C3)S(C)(=O)=O)cc2nn1-c1ccc(Cl)cc1]

To a solution of Compound (6) (27 mg, 0.05 mmol) in MeOH (2 mL) was added, simultaneously, paraformaldehyde (30 mg) and sodium borohydride (30 mg). After 16 h at ambient temperature water (25 ml) was added and the aqueous layer was extracted into EtOAc (3×30 mL). The combined organics were washed with brine (25 mL), dried (MgSO$_4$) and concentrated in vacuo to give a colourless oil (32 mg). The crude material was purified by reverse phase preparative LCMS: Acetonitrile/water (0.1% formic acid) to give Compound (7) (7.70 mg, 30%). ESI-MS m/z calculated for [M+H]$^+$: 516.2. found: 516.1. $^1$H NMR (400 MHz, CD$_3$CN, formate salt) δ 8.30 (s, 1H), 7.79 (s, 1H), 7.62-7.49 (m, 4H), 7.35 (s, 1H), 7.22 (br s, 1H), 3.84-3.70 (m, 2H), 3.70-3.56 (m, 2H), 3.38 (dd, J=16.0, 7.5 Hz, 2H), 3.07 (s, 3H), 2.89 (d, J=4.8 Hz, 3H), 2.75 (dt, J=15.4, 7.8 Hz, 1H), 2.51 (s, 3H), 2.35 (ddd, J=13.6, 8.1, 5.6 Hz, 1H), 1.87 (ddd, J=17.6, 11.0, 5.2 Hz, 2H), 1.11-0.98 (m, 3H), 0.65-0.57 (m, 1H).

Post-Coupling Functionalisation (N-Acylation)

6-{[2-(1-acetylazetidin-3-yl)ethyl](methylsulfonyl)amino}-2-(4-chlorophenyl)-5-cyclopropyl-N-methyl-2H-indazole-3-carboxamide (8)

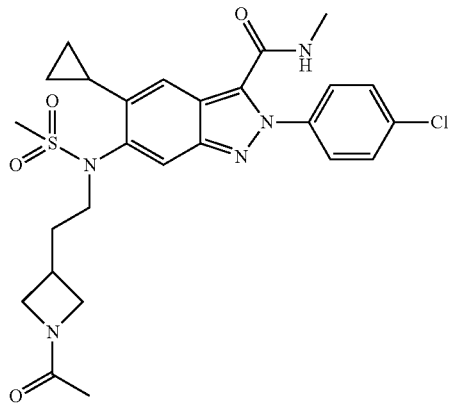 [SMILES: CNC(=O)c1c2cc(C3CC3)c(N(CCC3CN(C(C)=O)C3)S(C)(=O)=O)cc2nn1-c1ccc(Cl)cc1]

To a solution of Compound (6) (8 mg, 0.02 mmol) in DCM (2.0 mL) was added acetic anhydride (0.1 mL) and pyridine (0.1 mL) and the mixture was stirred at ambient temperature for 16 h. The reaction mixture was then concentrated in vacuo and the residue partitioned between EtOAc (25 mL) and water (15 mL). The organic layer was separated and the aqueous layer was extracted with EtOAc (3×15 mL). The combined organics were washed with brine (15 mL), dried (MgSO$_4$) and concentrated in vacuo (32 mg). The crude material was purified by reverse phase preparative LCMS: Acetonitrile/water (0.1% formic acid) to give Compound (8) (2.14 mg, 20%). ESI-MS m/z calculated for [M+H]$^+$: 544.2. found: 544.1. $^1$H NMR (400 MHz, CD$_3$CN) δ 7.85 (s, 1H), 7.63-7.54 (m, 4H), 7.40 (s, 1H), 7.05 (br s, 1H), 4.21-4.14 (m, 1H), 3.93 (td, J=8.9, 3.2 Hz, 1H), 3.76-3.67 (m, 3H), 3.49-3.43 (m, 1H), 3.11 (d, J=1.0 Hz, 3H), 2.93 (d, J=4.8 Hz, 3H), 2.77-2.64 (m, 1H), 2.46-2.36 (m, 1H), 1.95-1.81 (m, 2H), 1.73 (d, J=2.4 Hz, 3H), 1.14-1.02 (m, 3H), 0.69-0.58 (m, 1H).

Post-Coupling Ring Formation

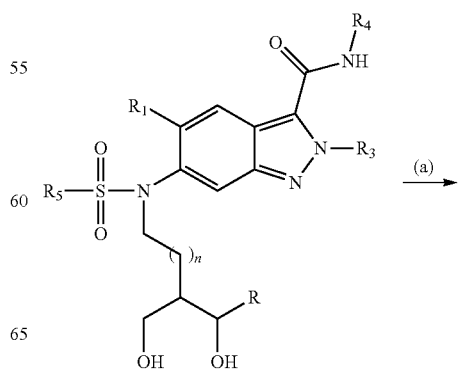

-continued

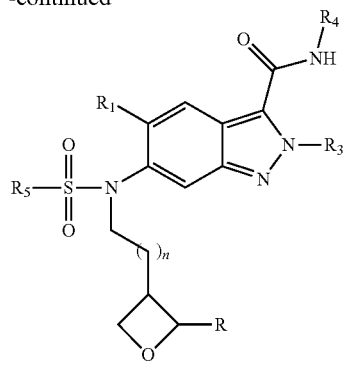

Scheme 5: where R is an optional substituent as previously defined n is an integer 0, 1, 2, 3, 4 or 5 and each $(CH_2)_n$ moiety when present may be independently optionally substituted with one or two substituents.

Step a)

The diol, formed by coupling a suitable triol precursor to a sulphonamide of formula (II) under Mitsunobu conditions, was dissolved in a suitable solvent (e.g. THF) and treated with a suitable base (e.g. potassium tert-butoxide) followed by p-toluenesulfonyl chloride to give, upon work-up, the corresponding oxetane.

2-(4-Chlorophenyl)-5-cyclopropyl-N-methyl-6-[{2-[-2-methyloxetan-3-yl]ethyl}(methylsulfonyl)amino]-2H-indazole-3-carboxamide (9)

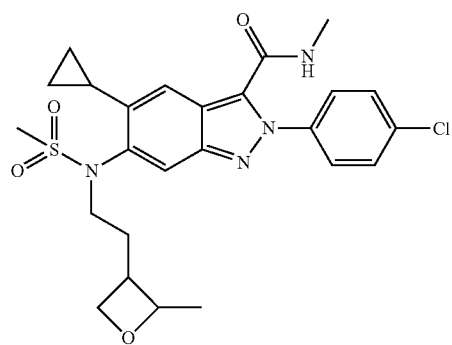 [SMILES: CNC(=O)c1c2cc(C3CC3)c(N(CCC3COC3C)S(C)(=O)=O)cc2nn1-c1ccc(Cl)cc1]

2-(4-Chlorophenyl)-5-cyclopropyl-6-{[4-hydroxy-3-(hydroxymethyl)pentyl](methylsulfonyl)amino}-N-methyl-2H-indazole-3-carboxamide was prepared by alkylating 2-(4-chlorophenyl)-5-cyclopropyl-N-methyl-6-[(methylsulfonyl)amino]-2H-indazole-3-carboxamide (i) with (±)-3-(hydroxymethyl)pentane-1,4-diol (prepared from (±)-3-acetyldihydrofuran-2(3H)-one as described by T. Mitsuhiro, Yanagihara, Hiroko and Y. Sachiko, *Heterocycles*, 1992 33, 489-492). Then, to a solution of Compound (i) (240 mg, 0.45 mmol) in anhydrous THF (35 mL) at 0° C. under argon was added potassium tert-butoxide (60 mg, 0.53 mmol) in several portions (the reaction mixture became yellow in colour) followed by a solution of p-toluenesulfonyl chloride (95 mg, 0.50 mmol) in anhydrous THF (10 mL), which was added dropwise over 10 min. The reaction was warmed to RT and monitored by TLC/LCMS and then cooled to at 0° C. whereupon more potassium tert-butoxide (80 mg, 0.71 mmol) was added. The reaction mixture was then warmed to RT and stirred for 17 h after which time, aq. saturated ammonium chloride solution was added (20 mL) and the organics extracted into Et$_2$O (3×100 mL), dried (MgSO$_4$) and concentrated in vacuo. Purification by automated column chromatography (Biotage SP4, Reveleris 4 g, silica gel cartridge) eluting with EtOAc:n-hepatane (gradient elution, 50% to 100% v/v) and then again by automated column chromatography (Biotage SP4, SNAP KP-C18-HS 30 g, reverse phase) eluting with ACN:water (gradient elution, 0-100% v/v) gave Compound (9) as the trans isomer (mixture of enantiomeric compounds (32) and (33)) (99 mg, 43%). $^1$H NMR (400 MHz, CDCl$_3$) δ 7.70 (s, 1H), 7.56-7.48 (m, 4H), 7.37 (s, 1H), 5.88-5.82 (m, 1H), 4.62-4.47 (m, 2H), 4.24-4.15 (m, 1H), 3.62 (t, J=7.9 Hz, 2H), 3.04 (s, 3H), 2.99 (d, J=4.9 Hz, 3H), 2.67-2.53 (m, 1H), 2.45-2.33 (m, 1H), 2.06-1.82 (m, 2H), 1.39 (d, J=6.1 Hz, 1.5H), 1.36 (d, J=6.1 Hz, 1.5H), 1.17-1.04 (m, 2H), 1.04-0.93 (m, 1H), 0.66-0.54 (m, 1H). ESI-MS m/z calculated for [M+H]$^+$: 517.2. found: 517.0.

2-(4-chlorophenyl)-5-cyclopropyl-6-[2-(3-hydroxyazetidin-1-yl)ethyl-methylsulfonyl-amino]-N-methyl-indazole-3-carboxamide (22)

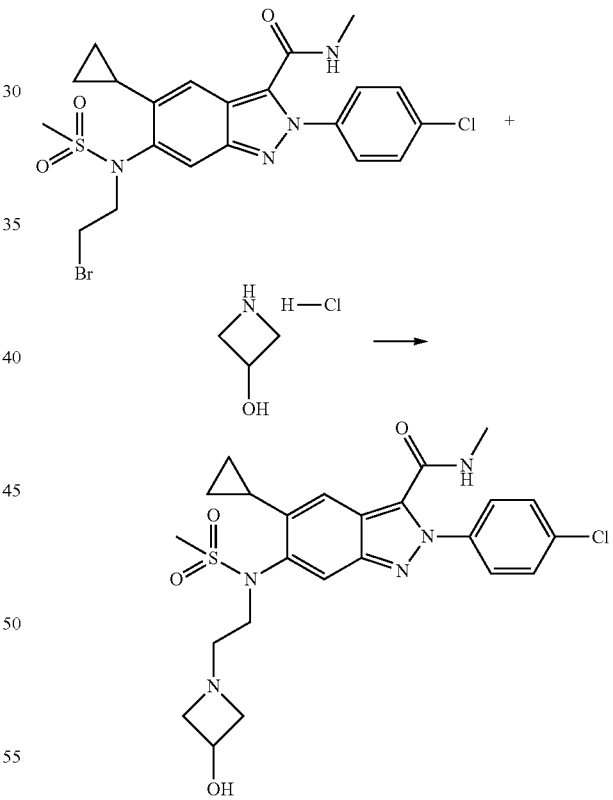

To a stirred solution of 6-[2-bromoethyl(methylsulfonyl)amino]-2-(4-chlorophenyl)-5-cyclopropyl-N-methyl-indazole-3-carboxamide (5 mg, 0.01 mmol) in MeCN (500 uL) was added azetidin-3-ol hydrochloride (6.6 mg, 0.06 mmol) followed by potassium carbonate (6 mg). The resultant suspension was heated at 65 deg C. in a sealed vial and after 3 days, cooled to RT then filtered through a cotton wool plug. The residue was washed with MeCN (2 mL) and the volatiles removed in vacuo. The residual colourless oil was purified by preparative HPLC/MS (MeCN/0.1% formic acid in water (v/v)—gradient elution) to give Compound (22) as a white amorphous solid (4.5 mg, 91%). $^1$H NMR (400 MHz, CD$_3$CN) δ 7.90 (s, 1H), 7.63-7.53 (m, 4H), 7.42 (s, 1H), 7.03 (br s, 1H), 4.67-4.40 (m, 2H), 4.17 (br s, 2H), 3.96 (br s, 2H), 3.80 (br s, 1H), 3.38 (br s, J=41.2 Hz, 2H), 3.16 (s, 3H), 2.91 (d, J=4.8 Hz, 3H), 2.34-2.33 (m, 1H), 1.18-1.01 (m, 3H), 0.68-0.58 (m, 1H). ESI-MS m/z calculated for [M+H]$^+$: 518.16. found: 518.10.

The following compounds were similarly prepared by reference to the general method(s) and/or examples previously described.

TABLE 1

Compounds and characterisation data

| No | Observed LCMS m/z [M + H]$^+$ | $^1$H NMR |
|---|---|---|
| 10 | 503.0. | (400 MHz, CD$_3$CN) δ 7.81 (s, 1H), 7.61-7.50 (m, 4H), 7.36 (s, 1H), 6.98 (br s, 1H), 4.71-4.61 (m, 2H), 4.30-4.19 (m, 2H), 3.67-3.59 (m, 2H), 3.13-2.99 (m, 4H), 2.89 (d, J = 4.8 Hz, 3H), 2.43-2.31 (m, 1H), 2.02-1.85 (m, 2H), 1.11-0.97 (m, 3H), 0.66-0.56 (m, 1H). |
| 11 | 517.0. | (400 MHz, CD$_3$CN) δ 7.83 (d, J = 0.5 Hz, 1H), 7.61-7.50 (m, 4H), 7.38 (s, 1H), 7.03-6.93 (m, 1H), 4.31-4.18 (m, 4H), 3.81-3.61 (m, 2H), 3.09 (s, 3H), 2.89 (d, J = 4.8 Hz, 3H), 2.43-2.32 (m, 1H), 2.07-1.86 (m, 2H), 1.24 (s, 3H), 1.12-0.97 (m, 3H), 0.66-0.56 (m, 1H). |
| 12 | 503.1. | (400 MHz, CD$_3$CN) δ 7.91-7.86 (m, 1H), 7.60-7.48 (m, 4H), 7.27 (s, 1H), 6.98 (s, 1H), 4.27 (d, J = 6.0 Hz, 1H), 4.21-4.12 (m, 4H), 4.04-3.98 (m, 1H), 3.07 (s, 3H), 2.89 (d, J = 4.8 Hz, 3H), 2.41 (tt, J = 8.1, 5.5 Hz, 1H), 1.36 (s, 3H), 1.16-1.01 (m, 3H), 0.69-0.60 (m, 1H). |
| 13 | 503.0. | (400 MHz, CD$_3$CN) δ 7.86 (d, J = 5.5 Hz, 1H), 7.65-7.54 (m, 4H), 7.40 (s, 1H), 7.02 (br s, 1H), 4.94-4.79 (m, 1H), 4.63-4.53 (m, 1H), 4.49-4.38 (m, 1H), 3.89-3.70 (m, 2H), 3.12 (s, 3H), 2.93 (d, J = 4.8 Hz, 3H), 2.73-2.61 (m, 1H), 2.46-2.28 (m, 2H), 2.10-1.84 (m, 2H), 1.16-1.01 (m, 3H), 0.70-0.59 (m, 1H). |
| 14 | 489.0. | (400 MHz, CD$_3$CN) δ 7.79 (d, J = 0.6 Hz, 1H), 7.59-7.51 (m, 4H), 7.31 (s, 1H), 6.97 (s, 1H), 4.63 (dd, J = 7.5, 6.2 Hz, 1H), 4.56 (dd, J = 7.7, 6.3 Hz, 1H), 4.31 (t, J = 6.0 Hz, 1H), 4.22-4.12 (m, 2H), 3.98 (dd, J = 13.6, 6.3 Hz, 1H), 3.22-3.05 (m, 4H), 2.89 (d, J = 4.8 Hz, 3H), 2.32-2.20 (m, 1H), 1.13-0.95 (m, 3H), 0.69-0.58 (m, 1H). |
| 15 | 517.0. | (400 MHz, CD$_3$CN, ca 1:1 rotamers) δ 7.87 (d, J = 0.4 Hz, 1H), 7.81 (d, J = 0.5 Hz, 1H), 7.61-7.50 (m, 8H), 7.35-7.31 (m, 2H), 6.99 (br s, 2H), 4.65-4.56 (m, 3H), 4.54-4.47 (m, 1H), 4.33 (t, J = 6.2 Hz, 1H), 4.30-4.21 (m, 2H), 4.11 (t, J = 6.3 Hz, 1H), 3.69-3.60 (m, 1H), 3.58-3.42 (m, 3H), 3.04 (d, J = 9.4 Hz, 6H), 3.02-2.95 (m, 1H), 2.89 (dd, J = 4.8, 1.5 Hz, 6H), 2.87-2.76 (m, 1H), 2.54-2.44 (m, 7H), 2.44-2.34 (m, 1H), 1.96-1.90 (m, 2H), 1.14-1.04 (m, 6H), 0.69-0.59 (m, 2H). |
| 16 | 545.0. | (400 MHz, CDCl$_3$) δ 7.79 (s, 1H), 7.58-7.48 (m, 4H), 7.40 (s, 1H), 5.79 (br d, J = 4.1 Hz, 1H), 4.43 (t, J = 6.6 Hz, 2H), 4.30 (d, J = 6.2 Hz, 1H), 4.24 (d, J = 6.2 Hz, 1H), 4.06-3.86 (m, 2H), 3.08 (s, 3H), 3.01 (d, J = 4.9 Hz, 3H), 2.49-2.41 (m, 1H), 2.07-1.82 (m, 3H), 1.15-1.07 (m, 2H), 1.06-1.00 (m, 1H), 0.85 (d, J = 7.1 Hz, 3H), 0.83 (d, J = 7.1 Hz, 3H), 0.61-0.55 (m, 1H). |
| 17 | 517.0. | (400 MHz, CDCl$_3$) δ 7.76 (s, 0.5H), 7.75 (s, 0.5H), 7.57-7.48 (m, 4H), 7.38 (s, 1H), 5.85-5.77 (m, 1H), 4.62-4.51 (m, 1H), 4.48-4.38 (m, 1H), 4.27-4.16 (m, 1H), 3.91-3.70 (m, 2H), 3.07 (s, 1.5H), 3.07 (s, 1.5H), 3.01 (d, J = 4.9 Hz, 3H), 2.74-2.58 (m, 1H), 2.47-2.33 (m, 1H), 2.22-2.11 (m, 0.5H), 2.11-2.01 (m, 0.5H), 2.01-1.87 (m, 1H), 1.19 (d, J = 6.8 Hz, 1.5H), 1.18 (d, J = 6.8 Hz, 1.5H), 1.13-1.05 (m, 2H), 1.04-0.94 (m, 1H), 0.66-0.56 (m, 1H). |
| 18 | 521.2. | (400 MHz, CD$_3$CN; ca 3:2 rotamers) δ 7.88-7.82 (m, 2H), 7.61-7.50 (m, 8H), 7.41 (s, 1H), 7.37 (s, 1H), 6.98 (br s, 2H), 5.05-4.96 (m, 1H), 4.93-4.83 (m, 1H), 4.71-4.60 (m, 5H), 4.58 (t, J = 6.2 Hz, 1H), 4.52 (t, J = 6.1 Hz, 1H), 4.39-4.32 (m, 2H), 4.07-3.96 (m, 1H), 3.89-3.78 (m, 1H), 3.72-3.57 (m, 1H), 3.38-3.20 (m, 2H), 3.16 (s, 3H), 3.11 (s, 3H), 2.89 (d, J = 4.8 Hz, 6H), 2.43-2.34 (m, 1H), 2.34-2.25 (m, 1H), 1.12-0.96 (m, 6H), 0.74-0.66 (m, 1H), 0.65-0.55 (m, 1H). |
| 19 | 624.1 | (400 MHz, CD$_3$CN) δ 7.83 (s, 1H), 7.62-7.53 (m, 4H), 7.38 (s, 1H), 7.00 (br s, 1H), 3.92 (d, J = 4.0 Hz, 2H), 3.73-3.62 (m, 2H), 3.50-3.40 (m, 2H), 3.09 (s, 3H), 2.91 (d, J = 4.8 Hz, 3H), 2.69-2.57 (m, 1H), 2.43-2.34 (m, 1H), 1.93-1.76 (m, 2H), 1.38 (s, 9H), 1.11-1.01 (m, 3H), 0.66-0.56 (m, 1H). |
| 20 | 498.2 | (400 MHz, CDCl$_3$) δ 8.52 (s, 1H), 8.36 (s, 1H), 7.79 (d, J = 0.9 Hz, 2H), 7.71 (s, 1H), 7.55 (s, 0.5H), 7.55 (s, 0.5H), 4.62-4.49 (m, 2H), 4.28-4.17 (m, 1H), 3.73-3.53 (m, 2H), 3.06-3.04 (m, 6H), 2.68-2.56 (m, 1H), 2.47 (s, 3H), 2.35-2.24 (m, 1H), 2.07-1.86 (m, 2H), 1.39 (d, J = 6.1 Hz, 1.5H), 1.36 (d, J = 6.1 Hz, 1.5H), 1.09-0.98 (m, 2H), 0.97-0.87 (m, 1H), 0.64-0.53 (m, 1H). |
| 21 | 498.2 | (400 MHz, CDCl$_3$) δ 8.64-8.52 (m, 1H), 8.40-8.34 (m, 1H), 7.84-7.70 (m, 3H), 7.50 (s, 1H), 4.44-4.29 (m, 4H), 3.85-3.63 (m, 2H), 3.09 (s, 3H), 3.07 (d, J = 4 Hz, 3H), 2.48 (s, 3H), 2.34-2.23 (m, 1H), 2.15-1.94 (m, 2H), 1.28 (s, 3H), 1.07-0.96 (m, 2H), 0.92-0.82 (m, 1H), 0.60-0.46 (m, 1H). |

TABLE 1-continued

Compounds and characterisation data

| No | Observed LCMS m/z [M + H]+ | 1H NMR |
|---|---|---|
| 23 | 420.0 | (400 MHz, DMSO) δ 9.19 (s, 1H), 8.64-8.56 (m, 2H), 8.21 (dd, J = 8.7, 2.6 Hz, 1H), 7.95 (d, J = 8.7, 0.6 Hz, 1H), 7.66 (d, 1H), 7.34 (s, 1H), 3.11 (s, 3H), 2.82 (d, J = 4.7 Hz, 3H), 2.32-2.20 (m, 1H), 1.04-0.93 (m, 2H), 0.75-0.66 (m, 2H). |
| 24 | 583.1 | (400 MHz, CD3CN) δ 8.39-8.33 (m, 1H), 7.89-7.82 (m, 1H), 7.80 (s, 1H), 7.75 (d, J = 8.2 Hz, 1H), 7.37 (br s, 1H), 7.34 (s, 1H), 3.96-3.87 (m, 2H), 3.70-3.64 (m, 2H), 3.53-3.40 (m, 2H), 3.09 (s, 3H), 2.93 (d, J = 4.8 Hz, 3H), 2.68-2.58 (m, 1H), 2.44 (s, 3H), 2.41-2.29 (m, 1H), 1.92-1.77 (m, 2H), 1.37 (s, 9H), 1.11-0.94 (m, 3H), 0.61-0.49 (m, 1H). |
| 25 | 525.2 | (400 MHz, CD3CN) δ 8.39-8.33 (m, 1H), 7.89-7.83 (m, 1H), 7.81 (s, 1H), 7.75 (d, J = 8.2 Hz, 1H), 7.41-7.32 (m, 2H), 4.20-4.12 (m, 1H), 3.95-3.87 (m, 1H), 3.73-3.66 (m, 3H), 3.49-3.41 (m, 1H), 3.10 (s, 3H), 2.93 (d, J = 4.8 Hz, 3H), 2.74-2.62 (m, 1H), 2.44 (s, 3H), 2.42-2.32 (m, 1H), 1.86 (ddd, J = 14.4, 13.5, 7.1 Hz, 2H), 1.71 (d, J = 1.8 Hz, 3H), 1.11-0.96 (m, 3H), 0.60-0.52 (m, 1H). |
| 26 | 521.2 | (400 MHz, CD3CN) δ 7.83 (s, 1H), 7.61-7.50 (m, 4H), 7.39 (s, 1H), 7.00 (br s, 1H), 4.70-4.43 (m, 4H), 3.88-3.74 (m, 2H), 3.10 (s, 3H), 2.89 (d, J = 4.8 Hz, 3H), 2.41-2.26 (m, 3H), 1.11-1.00 (m, 3H), 0.66-0.57 (m, 1H). |
| 27 | 631.7 | (400 MHz, CD3CN) δ 7.84 (d, J = 0.5 Hz, 1H), 7.63-7.47 (m, 4H), 7.38 (s, 1H), 7.01 (s, 1H), 3.81-3.63 (m, 4H), 3.57 (d, J = 9.1 Hz, 2H), 3.13 (s, 3H), 3.09 (s, 3H), 2.93-2.86 (m, 3H), 2.41-2.29 (m, 1H), 2.27-2.19 (m, 2H), 1.34 (s, 9H), 1.13-0.98 (m, 3H), 0.65-0.54 (m, 1H). |
| 28 | 514.2 | (400 MHz, CDCl3) δ 8.56 (d, J = 4.6 Hz, 1H), 8.37 (s, 1H), 7.83-7.77 (m, 2H), 7.76 (t, J = 2.3 Hz, 1H), 7.54 (d, J = 9.1 Hz, 1H), 4.65 (d, J = 6.8 Hz, 2H), 4.33 (t, J = 6.7 Hz, 2H), 3.83-3.64 (m, 3H), 3.21 (s, 3H), 3.11-3.02 (m, 6H), 2.48 (s, 3H), 2.42-2.23 (m, 3H), 1.09-0.99 (m, 2H), 0.97-0.85 (m, 1H), 0.63-0.51 (m, 1H). |
| 29 | 532.0 | (400 MHz, DMSO) δ 8.76-8.66 (m, 1H), 8.27 (s, 1H), 8.01 (s, 1H), 7.70-7.55 (m, 4H), 7.31 (s, 1H), 3.72-3.54 (m, 4H), 3.29-3.22 (m, 2H), 3.17 (s, 3H), 3.07 (s, 3H), 2.83 (d, J = 4.6 Hz, 3H), 2.39-2.27 (m, 1H), 2.21-2.07 (m, 1H), 2.00 (dt, J = 13.8, 7.4 Hz, 1H), 1.08-0.93 (m, 3H), 0.56 (dd, J = 11.0, 5.5 Hz, 1H). |
| 30 | 574.1 | (400 MHz, CD3CN) δ 7.87 (d, J = 3.6 Hz, 1H), 7.65-7.54 (m, 4H), 7.42 (s, 1H), 7.05 (s, 1H), 4.07-3.98 (m, 1H), 3.90-3.82 (m, 1H), 3.81-3.71 (m, 3H), 3.62 (d, J = 10.2 Hz, 1H), 3.17 (s, 3H), 3.14 (d, J = 2.3 Hz, 3H), 2.92 (t, J = 5.4 Hz, 3H), 2.45-2.35 (m, 1H), 2.28-2.12 (m, 2H), 1.76 (s, 3H), 1.17-1.00 (m, 3H), 0.71-0.59 (m, 1H). |
| 31 | 516.94 | (400 MHz, CDCl3) δ 7.72 (s, 1H), 7.56-7.48 (m, 4H), 7.37 (s, 1H), 5.92-5.83 (m, 1H), 5.07-4.97 (m, 1H), 4.75-4.66 (m, 1H), 4.15-4.06 (m, 1H), 3.70-3.52 (m, 2H), 3.04 (s, 3H), 2.99 (d, J = 4.9 Hz, 3H), 2.97-2.88 (m, 1H), 2.49-2.34 (m, 1H), 2.05-1.85 (m, 2H), 1.24 (d, J = 6.5 Hz, 1.5H), 1.23 (d, J = 6.5 Hz, 1.5H), 1.15-0.98 (m, 3H), 0.63-0.48 (m, 1H). |
| 32[a] | 516.9 | (400 MHz, CDCl3) δ 7.78 (s, 1H), 7.62-7.53 (m, 4H), 7.44 (s, 1H), 5.81 (s, 1H), 4.66-4.53 (m, 2H), 4.30-4.21 (m, 1H), 3.74-3.62 (m, 2H), 3.09 (s, 3H), 3.05 (d, J = 5.7 Hz, 3H), 2.72-2.59 (m, 1H), 2.51-2.38 (m, 1H), 2.13-1.89 (m, 2H), 1.43 (dd, J = 9.9, 6.1 Hz, 3H), 1.21-1.10 (m, 2H), 1.09-1.00 (m, 1H), 0.65 (dt, J = 9.0, 5.5 Hz, 1H). |
| 33[b] | 516.9 | (400 MHz, CDCl3) δ 7.78 (s, 1H), 7.62-7.53 (m, 4H), 7.44 (s, 1H), 5.81 (s, 1H), 4.66-4.53 (m, 2H), 4.30-4.21 (m, 1H), 3.74-3.62 (m, 2H), 3.09 (s, 3H), 3.05 (d, J = 5.7 Hz, 3H), 2.72-2.59 (m, 1H), 2.51-2.38 (m, 1H), 2.13-1.89 (m, 2H), 1.43 (dd, J = 9.9, 6.1 Hz, 3H), 1.21-1.10 (m, 2H), 1.09-1.00 (m, 1H), 0.65 (dt, J = 9.0, 5.5 Hz, 1H). |
| 34 | 504.0 | (400 MHz, CDCl3) δ 8.53 (s, 1H), 7.98 (s, 2H), 7.77 (s, 1H), 7.52 (s, 1H), 7.38 (s, 1H), 4.89-4.76 (m, 2H), 4.43-4.32 (m, 2H), 3.81-3.61 (m, 2H), 3.12 (d, J = 6.9 Hz, 3H), 3.09 (s, 3H), 2.45-2.31 (m, 1H), 2.17-1.96 (m, 3H), 1.19-1.00 (m, 3H), 0.73-0.61 (m, 1H). |
| 35 | 613.0 | (400 MHz, CD3CN) δ 8.34 (dd, J = 1.5, 0.7 Hz, 1H), 7.86-7.72 (m, 3H), 7.37 (s, 1H), 7.28 (br s, 1H), 5.46 (br m, 1H), 4.35-4.28 (m, 2H), 4.28-4.22 (m, 2H), 3.85-3.72 (m, 2H), 3.27 (d, J = 6.4 Hz, 2H), 3.11 (s, 3H), 2.91 (d, J = 4.8 Hz, 3H), 2.42 (s, 3H), 2.39-2.30 (m, 1H), 2.06-1.87 (m, 2H), 1.26 (s, 9H), 1.09-0.95 (m, 3H), 0.65-0.56 (m, 1H). |
| 36 | 533.0 | (400 MHz, CDCl3) δ 7.77 (s, 1H), 7.60-7.47 (m, 4H), 7.41 (s, 1H), 5.81 (d, J = 4.4 Hz, 1H), 4.66 (t, J = 6.1 Hz, 2H), 4.30 (t, J = 6.1 Hz, 2H), 3.84-3.64 (m, 2H), 3.23 (s, 3H), 3.07 (s, 3H), 3.02 (t, J = 6.1 Hz, 3H), 2.48-2.31 (m, 2H), 2.30-2.15 (m, 2H), 1.18-1.06 (m, 2H), 1.06-0.96 (m, 1H), 0.68-0.57 (m, 1H). |

[a]Unknown absolute stereochemistry, nominally assigned as (2S,3R) enantiomer.
[b]Unknown absolute stereochemistry, nominally assigned as (2R,3S) enantiomer.

Biological Data

The in vitro antiviral activity of the compounds of the invention may be determined using the following protocols.

HCV Polymerase Inhibition Assay

HCV polymerase reactions were carried out using a modified method of Howe et al., *Antimicrobial Agents and Chemotherapy* 2004 48(12): 4813-4821. Reactions contained a final concentration of, 0.5% DMSO, 100 nM 1b (BK) NS5BΔ21, 20 mM Tris-HCl pH 7.5, 5 mM $MgCl_2$, 5 mM $MnCl_2$, 3 mM DTT, 0.05% BSA, 0.2 U/µL RNasin, 10 µg/mL Poly(rC) template, GTP (at Km) and 0.05 µCi/µL $^{33}$P-GTP in a total reaction volume of 50 µL. Compounds were tested in a three fold dilution series, for example starting from 50 µM. Reactions were initiated with the addition of GTP and terminated after 90 min with 50 µL ice cold 0.2M EDTA. Terminated reactions were transferred to DEAE 96-well filter plates, unincorporated nucleotides washed from the filters and 50 µL scintillation fluid added prior to reading on a scintillation counter. The compound concentration that reduced $^{33}$P-GTP incorporation by 50% ($IC_{50}$) was calculated using non-linear regression.

Representative 1b polymerase $IC_{50}$ (µM) values for selected compounds of the invention in the HCV polymerase inhibition assay are listed as follows where $IC_{50}$ (µM) values lie in the ranges:

A (<0.10 µM): 3, 4, 10, 11, 16, 18, 26
B (0.1-0.49 µM): 6, 7, 8, 9, 13, 14, 15, 17, 19, 21,28, 31,32, 33, 34
C (0.5-0.99 µM): 5, 20, 22, 25, 27, 30
D (1.0-10.0 µM): 12, 24, 29

HCV Replicon Assays

A genotype 1b (Con 1) subgenomic replicon cell line based on Blight et al., *Science* 2000 290: 1972-1974, modified to express a *Renilla* luciferase reporter gene was used to assess antiviral activity of test compounds. Cell cultures were maintained in a sub-confluent state in DMEM with glutamine, 10% heat-inactivated foetal bovine serum (FBS) and G418 (Geneticin®).

For assay, cells were seeded at a density of 7000 cells/well into 96 well tissue culture trays in culture media lacking G418. Compounds were tested in a three fold dilution series, for example starting from 50 uM. After 72 hours incubation at 37° C. and 5% $CO_2$, *Renilla* luciferase activity was quantified via the Promega *Renilla* Luciferase or Renilla-Glo™ Luciferase Assay Systems (Promega corporation. The same method was employed for replicon assays using subgenomic genotype 1a (H77) and 2a (JFH-1) replicon cell lines with a seeding cell density of 5000 cells/well for the 2a cell lines.

The compound concentration that reduced luciferase activity by 50% ($EC_{50}$) was calculated using non-linear regression. Representative genotype 1b $EC_{50}$ values for selected compounds of the invention are listed as follows where $EC_{50}$ (µM) values lie in the ranges:

A (<0.10 µM): 3, 4, 5, 8, 9, 10, 11, 13, 14, 16, 19, 20, 21, 24, 26, 27, 28, 31,32, 33, 34
B (0.1-0.49 µM): 7, 17, 18, 22, 25, 36
C (0.5-0.99 µM): 15, 30
D (1.0-10.0 µM): 6, 12, 29, 35

Cytotoxicity Analysis

Cytotoxicity of compounds against genotype 1b replicon cells was determined via metabolism of the vital dye 3-(4,5-dimethylthiaxol-2-yl)-2,5-diphenyltetrazolium bromide (MTT, for example see Watanabe et al., *Journal of Virological Methods* 1994 48:257-265). Plates were prepared as described for the HCV Replicon assay and cytotoxicity of the test article was evaluated after three days. MTT was added to assay plates followed by three hour incubation at 37° C. Wells were aspirated to dryness and the formazan dye dissolved by the addition of isopropanol. Absorbance values were read at 5401690 nm). The compound concentration that reduced cell viability by 50% ($CC_{50}$) was calculated using non-linear regression. In general, compounds of the invention displayed low cytotoxicity with $CC_{50}$ values of >50 µM.

Cross-Genotype HCV Activity

Cross-genotypic activity of the compounds may be determined in HCV replicon assays for genotypes such as 1b, 1a and 2a as previously described and similarly for genotypes 3a, 4a, 5a, 6a and 7a. Multi-genotype HCV polymerase assays include genotypes such as 1b as previously described and similarly for genotypes 1a, 2a, 3a, 4a, 5a, 6a and 7a.

Combination Studies in Replicon Cells

A genotype 1b (Con 1) subgenomic replicon cell line based on Blight et al., *Science* 2000 290: 1972-1974, modified to express a *Renilla* luciferase reporter gene may be used to assess synergy of test compounds. Cell cultures were maintained in a sub-confluent state in DMEM with glutamine, 10% heat-inactivated foetal bovine serum (FBS) and G418 (Geneticin®).

For assay, cells are seeded at a density of 7000 cells/well into 96 well tissue culture trays in culture media lacking G418. The compound concentration that reduced luciferase activity by 50% ($EC_{50}$) is determined independently for each compound and used to set the range of concentrations for the combination experiments. Each compound is tested singly and in combination using either 3-fold or 5-fold serial dilutions above and below the $EC_{50}$. The ratio of the 2 compounds tested remained fixed across the titration range. Cytotoxicity of individual compounds is assessed independently and the titration range below the compound concentration that reduced cell viability by 50% ($CC_{50}$). After 72 hours incubation at 37° C. and 5% $CO_2$, *Renilla* luciferase activity is quantified via the Promega *Renilla* Luciferase Assay System.

Results are analysed and levels of synergy assessed via generation of 3D synergy plots using either MacSynergy™ II (Prichard, M. N., K. R. Aseltine, and C. Shipman, Jr. 1993. MacSynergy II. Version 1.0. User's manual. University of Michigan, Ann Arbor.) or by calculation of a combination index (CI) using the CalcuSyn software package (version 2.1) which performs multiple drug dose-effect calculations using the Median Effect methods (Chou T-C. Drug Combinations Studies and Their Synergy Quantification Using the Chou-Talalay Method. *Cancer Research* 2010; 70 440-446.). This model allows the calculation of a combination index (CI) which is a quantitative definition of an additive effect (CI=1), synergism (CI<1) or antagonism (CI>1) for different drug combinations. Theoretical additive interactions are individually calculated from the dose-response curves for each compound used. This surface is subtracted from the actual dose-response curve to give regions of non-additive interactions. Combination indices can be expressed for different binary combinations of compounds at specific concentrations.

Aqueous Solubility

Test compounds prepared in DMSO were screened in duplicate over a range of concentrations (1.6-100 ug/mL) in different aqueous media (for example a pH6.5 buffers which are relevant to the stomach and upper regions of the small intestine and therefore important when predicting the amount of drug likely to be in solution following oral administration). Test compounds were serially diluted in 100% DMSO ranging from 10-0.16 mg/mL. These titrated DMSO stocks were then further diluted 1:100 with assay buffer and added to test plates (UV Star Griener 384 well plates), maintaining the DMSO concentration at 1%. The solubility concentration range was determined by interpreting NEPHELOstar laser nephelometery readings taken after a 30 minute incubation at 25° C. A compound is considered to have good solubility when the value is >25 ug/mL.

A representative example of the invention having an optionally substituted 4-membered heterocyclic moiety i.e. Compound (14) was selected for comparative solubility studies as against Compounds A-D below. Surprisingly, only Compound 14 was found to have good solubility at pH 6.5 as demonstrated by the results obtained and provided in Table 2 below. In comparison Compounds A-D were considered to be poorly soluble.

TABLE 2

Compounds and solubility at pH6.5

| No. | Structure | Solubility at pH6.5 (μ/mL) | Observed LCMS m/z [M + H]$^+$ and $^1$H NMR data |
| --- | --- | --- | --- |
| 14 | 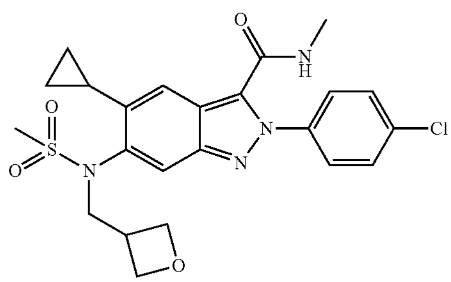 [SMILES: CNC(=O)c1c2cc(C3CC3)c(N(CC3COC3)S(C)(=O)=O)cc2nn1-c1ccc(Cl)cc1] | 25-50 | Refer to Table 1. |
| A | 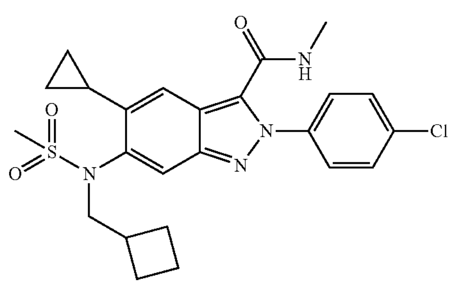 [SMILES: CNC(=O)c1c2cc(C3CC3)c(N(CC3CCC3)S(C)(=O)=O)cc2nn1-c1ccc(Cl)cc1] | 1.6-3.1 | ESI-MS m/z calculated for [M + H]$^+$: 487.2 found: 487.1. (400 MHz, CDCl$_3$): δ 7.70 (s, 1H), 7.55-7.49 (m, 4H), 7.32 (s, 1H), 5.77 (s, 1H), 3.78 (d, J = 7.5 Hz, 2H), 3.05 (s, 3H), 3.01 (d, J = 4.9 Hz, 3H), 2.53 (dt, J = 15.3, 7.7 Hz, 1H), 2.46-2.35 (m, 1H), 2.07-1.93 (m, 2H), 1.93-1.71 (m, 3H), 1.71-1.61 (m, 1H), 1.22-1.05 (m, 2H), 0.99-0.85 (m, 1H), 0.71-0.62 (m, 1H) |
| B | 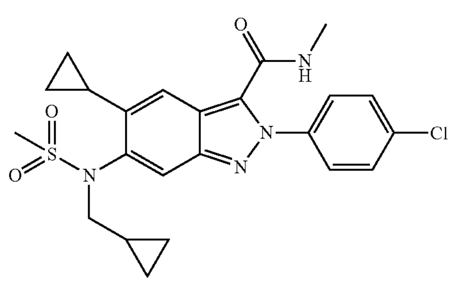 [SMILES: CNC(=O)c1c2cc(C3CC3)c(N(CC3CC3)S(C)(=O)=O)cc2nn1-c1ccc(Cl)cc1] | 3.1-6.3 | ESI-MS m/z calculated for [M + H]$^+$: 473.1; found: 473.1. $^1$H NMR (400 MHz, CDCl$_3$) δ 7.84 (s, 1H), 7.64-7.51 (m, 4H), 7.42 (s, 1H), 5.86 (brs, 1H), 3.66 (ddd, J = 20.9, 14.2, 7.2 Hz, 2H), 3.16 (s, 3H), 3.06 (d, J = 4.9 Hz, 3H), 2.56-2.44 (m, 1H), 1.20-1.06 (m, 3H), 1.04-0.96 (m, 1H), 0.72-0.61 (m, 1H), 0.57 (d, J = 7.9 Hz, 2H), 0.30-0.21 (m, 2H). |
| C | 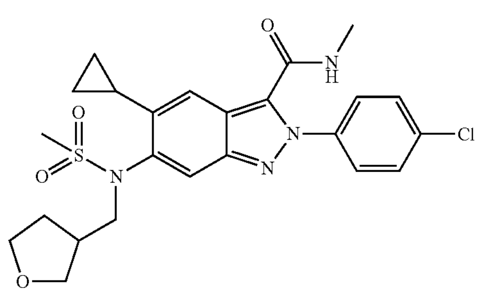 [SMILES: CNC(=O)c1c2cc(C3CC3)c(N(CC3CCOC3)S(C)(=O)=O)cc2nn1-c1ccc(Cl)cc1] | <1.6 | ESI-MS m/z calculated for [M + H]$^+$: 503.2; found: 503.0. $^1$H NMR (400 MHz, CDCl$_3$) δ 7.79 (d, J = 14.6 Hz, 1H), 7.64-7.50 (m, 4H), 7.39 (s, 1H), 5.82 (brs, 1H), 3.98-3.68 (m, 5H), 3.47 (dd, J = 8.9, 5.3 Hz, 1H), 3.09 (s, 3H), 3.05 (d, J = 4.9 Hz, 3H), 2.56-2.39 (m, 2H), 2.14-1.98 (m, 1H), 1.89 (dt, J = 20.1, 6.4 Hz, 1H), 1.24-1.09 (m, 2H), 1.09-1.00 (m, 1H), 0.74-0.67 (m, 1H). |

TABLE 2-continued

Compounds and solubility at pH6.5

| No. | Structure | Solubility at pH6.5 (μg/mL) | Observed LCMS m/z [M + H]+ and 1H NMR data |
|---|---|---|---|
| D | 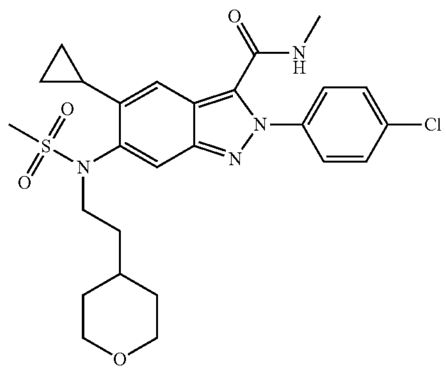 [SMILES: CNC(=O)c1c2cc(C3CC3)c(N(CCC3CCOCC3)S(C)(=O)=O)cc2nn1-c1ccc(Cl)cc1] | <1.6 | ESI-MS m/z calculated for [M + H]+: 531.2; found: 531.1. 1H NMR (400 MHz, CDCl3) δ 7.75 (s, 1H), 7.63-7.51 (m, 4H), 7.40 (s, 1H), 5.88 (brd, J = 4.5 Hz, 1H), 4.00-3.89 (m, 2H), 3.87-3.76 (m, 2H), 3.46-3.30 (m, 2H), 3.09 (s, 3H), 3.04 (d, J = 4.9 Hz, 3H), 2.52-2.39 (m, 1H), 1.71-1.49 (m, 5H), 1.39-1.20 (m, 2H), 1.20-0.99 (m, 3H), 0.70-0.58 (m, 1H). |

Representative solubility ranges at pH 6.5 for selected compounds of the invention are as follows:

A (12.5-25 μg/mL): 3, 20, 24, 29, 35
B (25-50 μg/mL): 8, 9, 26, 32
C (50-100 μg/mL): 17, 18, 28, 30, 33, 36
D (>100 μg/mL): 21, 25

Metabolic Stability Assay

The in vitro metabolic stability of compounds of the invention was tested using human liver microsomes as a preliminary indication of the likely in vivo metabolic clearance. The metabolic stability assay was performed by incubating test compounds individually (1 μM) with human liver microsomes at 37° C. and 0.4 mg/mL protein concentration. The metabolic reaction was initiated by the addition of an NADPH-regenerating system (i.e. NADPH is the cofactor required for CYP450-mediated metabolism) and quenched at various time points over the 60 min incubation period by the addition of acetonitrile. Additional samples with the dual co-factors, NADPH and UDPGA (the latter being the co-factor for glucuronidation), can be included in the incubation for qualitative assessment of the potential for glucuronide formation. Control samples (containing neither NADPH nor UDPGA) were included to monitor for potential degradation in the absence of cofactors. Concentrations of each test compound were determined by LC-MS or UPLC-MS relative to calibration standards. Test compound concentration versus time data were fitted to an exponential decay function to determine the first-order rate constant for substrate depletion. In cases where clear deviation from first-order kinetics was evident, only the initial linear portion of the profile was utilised to determine the degradation rate constant (k). Each substrate depletion rate constant can then be used to calculate: a degradation half-life, an in vitro intrinsic clearance value ($CL_{int}$, in vitro); a predicted in vivo hepatic intrinsic clearance value ($CL_{int}$) and a predicted in vivo hepatic extraction ratio ($E_H$). The predicted hepatic extraction ratios ($E_H$) obtained were used to classify compounds as low (<0.3), intermediate (0.3-0.7), high (0.7-0.95) or very high (>0.95) extraction compounds. A compound is considered to have good metabolic stability when the $E_H$ value is low or intermediate (i.e. $E_{H<0.7}$). Calculations, scaling parameters and classifications are essentially as described in the literature (for example see (1993) Physiological parameters in laboratory animal and humans. *Pharmaceutical Research*, 10:1093-1095; (Obach, 1999, *Drug Metab. Dispos.* 27: 1350-1359).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication, or information derived from it, or to any matter which is known, is not, and should not be taken as an acknowledgement or admission or any form of suggestion that prior publication, or information derived from it, or known matter forms part of the common general knowledge in the field of endeavour to which this specification relates.

The invention claimed is:

1. A compound of formula (I), salts, N-oxides, solvates, hydrates, racemates, enantiomers or diastereomers thereof:

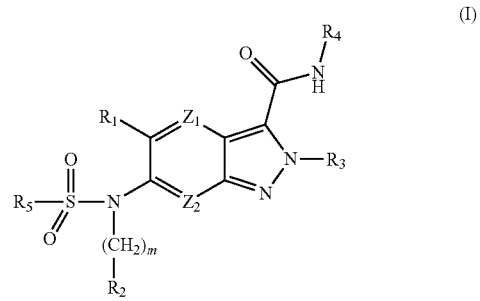

wherein $Z_1$ and $Z_2$ are each independently selected from the group consisting of C—H, C-halo, C—$C_{1-4}$alkyl, C—$C_{1-4}$alkylhalo, C—$C_{1-4}$alkoxy, C—$C_{1-4}$alkoxyhalo and N;

$R_1$ is selected from the group consisting of H, $C_{1-6}$alkyl, $C_{2-6}$alkenyl, $C_{2-6}$alkynyl, $C_{1-6}$alkoxy, halo, $C_{1-4}$alkylhalo, $C_{1-4}$alkoxyhalo, $C_{3-7}$cycloalkyl, $C_{3-7}$cycloalkenyl, 5-6-membered heterocyclyl and 5-6 membered heteroaryl and wherein alkyl, alkenyl, alkynyl, alkoxy, cycloalkyl, heterocyclyl and heteroaryl in each occurrence may be optionally substituted;

$R_2$ is an optionally substituted 4-membered heterocyclic ring;

$R_3$ is selected from the group consisting of aryl, aryl-X-aryl, aryl-X-heteroaryl, heteroaryl, heteroaryl-X-heteroaryl, and heteroaryl-X-aryl wherein X is $[C(R_5)_2]_p$, O, S, S(=O), $SO_2$, $NR_5$, C=O, $CF_2$, C(=O)$NR_5$ or $NR_5$C(=O) wherein p is 1, 2 or 3 and wherein aryl and heteroaryl in each occurrence may be optionally substituted;

$R_4$ is H, $C_{1-4}$alkyl, $C_{2-4}$alkenyl, $C_{2-4}$alkynyl, or $C_{3-7}$cycloalky, $R_5$ is independently H or optionally substituted $C_{1-6}$alkyl;

m represents an integer selected from the group consisting of 0, 1, 2, 3, 4, 5 and 6; and each ($CH_2$) moiety when present may be independently optionally substituted with one or two substituents; and further when m is an integer selected from the group consisting of 1, 2, 3, 4, 5 and 6 then one or more ($CH_2$) may be replaced with O, C=O, NH, optionally substituted N $C_{1-6}$alkyl, S, or $SO_2$.

2. A compound according to claim 1 wherein $R_2$ is an optionally substituted oxetane or azetidine ring.

3. A compound according to claim 1 which is of formula (Ia), salts, N-oxides, solvates, hydrates, racemates, enantiomers or diastereomers thereof:

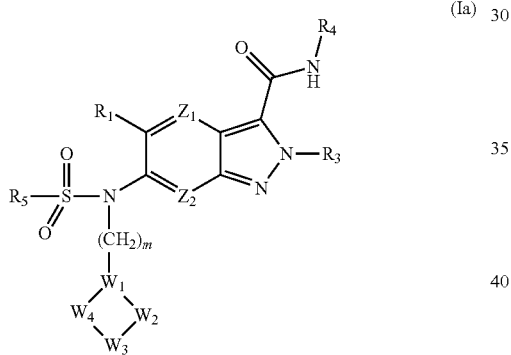

(Ia)

wherein $W_1$ is $CR^a$ or N;

$W_2$, $W_3$ and $W_4$ are each independently selected from the group consisting of O, $NR^b$, S, S=O, $SO_2$, C=O and $CR^cR^d$; and $R^a$, $R^b$, $R^c$ and $R^d$ are each independently selected from H or an optional substituent; and with the proviso that one of $W_1$, $W_2$, $W_3$ and $W_4$ is a heteroatom selected from the group consisting of O, $NR^b$ and S and the three remaining are independently $CR^a$ in the case of $W_1$ and $CR^cR^d$ in the case of any one of $W_2$, $W_3$ and $W_4$.

4. A compound according to claim 1 wherein $(CH)_m$ is an optionally substituted methylenyl, ethylenyl or propylenyl moiety.

5. A compound according to claim 1 selected from the group consisting of:

3) 5-cyclopropyl-N-methyl-2-(4-methylphenyl)-6-{(methylsulfonyl)[2-(oxetan-3-yl)ethyl]amino}-2H-indazole-3-carboxamide;

4) 2-(4-chlorophenyl)-5-cyclopropyl-N-methyl-6-{(methylsulfonyl)[3-(oxetan-2-yl)propyl]amino}-2H-indazole-3-carboxamide;

5) 5-cyclopropyl-N-methyl-2-(5-methylpyridin-2-yl)-6-{(methylsulfonyl)[2-(oxetan-3-yl)ethyl]amino}-2H-indazole-3-carboxamide;

6) 6-{[2-(azetidin-3-yl)ethyl](methylsulfonyl)amino}-2-(4-chlorophenyl)-5-cyclopropyl-N-methyl-2H-indazole-3-carboxamide;

7) 2-(4-chlorophenyl)-5-cyclopropyl-N-methyl-6-{[2-(1-methylazetidin-3-yl)ethyl](methylsulfonyl)amino}-2H-indazole-3-carboxamide;

8) 6-{[2-(1-acetylazetidin-3-yl)ethyl](methylsulfonyl)amino}-2-(4-chlorophenyl)-5-cyclopropyl-N-methyl-2H-indazole-3-carboxamide;

9) 2-(4-chlorophenyl)-5-cyclopropyl-N-methyl-6-{[2-(2-methyloxetan-3-yl)ethyl](methylsulfonyl)amino}-2H-indazole-3-carboxamide;

10) 2-(4-chlorophenyl)-5-cyclopropyl-N-methyl-6-{(methylsulfonyl)[2-(oxetan-3-yl)ethyl]amino}-2H-indazole-3-carboxamide;

11) 2-(4-chlorophenyl)-5-cyclopropyl-N-methyl-6-{[2-(3-methyloxetan-3-yl)ethyl](methylsulfonyl)amino}-2H-indazole-3-carboxamide;

12) 2-(4-chlorophenyl)-5-cyclopropyl-N-methyl-6-{[(3-methyloxetan-3-yl)methyl](methylsulfonyl)amino}-2H-indazole-3-carboxamide;

13) 2-(4-chlorophenyl)-5-cyclopropyl-N-methyl-6-{(methylsulfonyl)[2-(oxetan-2-yl)ethyl]amino}-2H-indazole-3-carboxamide;

14) 2-(4-chlorophenyl)-5-cyclopropyl-N-methyl-6-[(methylsulfonyl)(oxetan-3-ylmethyl)amino]-2H-indazole-3-carboxamide;

15) 2-(4-chlorophenyl)-5-cyclopropyl-N-methyl-6-{(methylsulfonyl)[2-(oxetan-3-yl)propyl]amino}-2H-indazole-3-carboxamide;

16) 2-(4-chlorophenyl)-5-cyclopropyl-N-methyl-6-[(methylsulfonyl) {2-[3-(propan-2-yl)oxetan-3-yl]ethyl}amino]-2H-indazole-3-carboxamide;

17) 3,5-anhydro-1-{[2-(4-chlorophenyl)-5-cyclopropyl-3-(methylcarbamoyl)-2H-indazol-6-yl](methylsulfonyl)amino}-1,2,4-trideoxy-4-methylpentitol;

18) 2-(4-chlorophenyl)-5-cyclopropyl-6-{[2-fluoro-2-(oxetan-3-yl)ethyl](methylsulfonyl)amino}-N-methyl-2H-indazole-3-carboxamide;

19) tert-butyl 3-(2-{[2-(4-chlorophenyl)-5-cyclopropyl-3-(methylcarbamoyl)-2H-indazol-6-yl](methylsulfonyl)amino}ethyl)azetidine-1-carboxylate;

20) 5-cyclopropyl-N-methyl-6-{[2-(2-methyloxetan-3-yl)ethyl](methylsulfonyl)amino}-2-(5-methylpyridin-2-yl)-2H-indazole-3-carboxamide;

21) 5-cyclopropyl-N-methyl-6-{[2-(3-methyloxetan-3-yl)ethyl](methylsulfonyl)amino}-2-(5-methylpyridin-2-yl)-2H-indazole-3-carboxamide;

22) 2-(4-chlorophenyl)-5-cyclopropyl-6-[2-(3-hydroxyazetidin-1-yl)ethyl-methylsulfonyl-amino]-N-methyl-indazole-3-carboxamide;

24) tert-butyl 3-[2-[[5-cyclopropyl-3-(methylcarbamoyl)-2-(5-methyl-2-pyridyl)indazol-6-yl]-methylsulfonyl-amino]ethyl]azetidine-1-carboxylate;

25) 6-[2-(1-acetylazetidin-3-yl)ethyl-methylsulfonyl-amino]-5-cyclopropyl-N-methyl-2-(5-methyl-2-pyridyl)indazole-3-carboxamide;

26) 2-(4-chlorophenyl)-5-cyclopropyl-6-[2-(3-fluorooxetan-3-yl)ethyl-methylsulfonyl-amino]-N-methyl-indazole-3-carboxamide;

27) tert-butyl 3-[2-[[2-(4-chlorophenyl)-5-cyclopropyl-3-(methylcarbamoyl)indazol-6-yl]-methylsulfonyl-amino]ethyl]-3-methoxy-azetidine-1-carboxylate;

28) 5-cyclopropyl-6-[2-(3-methoxyoxetan-3-yl)ethyl-methylsulfonyl-amino]-N-methyl-2-(5-methyl-2-pyridyl)indazole-3-carboxamide;
29) 2-(4-chlorophenyl)-5-cyclopropyl-6-[2-(3-methoxyazetidin-3-yl)ethyl-methylsulfonyl-amino]-N-methyl-indazole-3-carboxamide;
30) 6-[2-(1-acetyl-3-methoxy-azetidin-3-yl)ethyl-methylsulfonyl-amino]-2-(4-chlorophenyl)-5-cyclopropyl-N-methyl-indazole-3-carboxamide;
31) 2-(4-chlorophenyl)-5-cyclopropyl-N-methyl-6-[2-[-2-methyloxetan-3-yl]ethyl-methylsulfonyl-amino]indazole-3-carboxamide;
32) 2-(4-chlorophenyl)-5-cyclopropyl-N-methyl-6-[{2-[(2S,3R)-2-methyloxetan-3-yl]ethyl}(methylsulfonyl)amino]-2H-indazole-3-carboxamide;
33) 2-(4-chlorophenyl)-5-cyclopropyl-N-methyl-6-[{2-[(2R,3S)-2-methyloxetan-3-yl]ethyl}(methylsulfonyl)amino]-2H-indazole-3-carboxamide;
34) 2-(5-chloro-2-pyridyl)-5-cyclopropyl-N-methyl-6-[methylsulfonyl-[2-(oxetan-3-yl)ethyl]amino]indazole-3-carboxamide;
35) tert-butyl N-[[3-[2-[[5-cyclopropyl-3-(methylcarbamoyl)-2-(5-methyl-2-pyridyl)indazol-6-yl]-methylsulfonyl-amino]ethyl]oxetan-3-yl]methyl]carbamate;
36) 2-(4-chlorophenyl)-5-cyclopropyl-6-[2-(3-methoxyoxetan-3-yl)ethyl-methylsulfonyl-amino]-N-methyl-indazole-3-carboxamide; and salts, N-oxides, solvates, hydrates, racemates, enantiomers or diastereomers thereof.

6. A pharmaceutical agent comprising the compound according to claim 1 or salts, N-oxides, solvates, hydrates, racemates, enantiomers or diastereomers thereof and optionally another HCV antiviral agent.

7. A HCV polymerase inhibitor comprising the compound according to claim 1 or salts, N-oxides, solvates, hydrates, racemates, enantiomers or diastereomers thereof and optionally another HCV antiviral agent.

8. A pharmaceutical composition comprising the compound according to claim 1 or salts, N-oxides, solvates, hydrates, racemates, enantiomers or diastereomers thereof, a pharmaceutically acceptable carrier and optionally another HCV antiviral agent.

9. The pharmaceutical agent according to claim 6 additionally comprising at least one immunomodulatory agent.

10. The pharmaceutical agent according to claim 6 wherein the HCV antiviral agent is selected from the group consisting of Ribavarin, an NS5B inhibitor, an NS3/4A protease inhibitor and an NS5A inhibitor.

11. The pharmaceutical agent according to claim 6 adapted for oral administration.

12. A method for the treatment of a Flaviviridae viral infection which comprises administering an effective amount of the compound according to claim 1 or salts, N-oxides, solvates, hydrates, racemates, enantiomers or diastereomers thereof and optionally another HCV antiviral agent to a subject in need thereof.

13. The method according to claim 12 wherein the administration is oral administration.

14. The method according to claim 12 wherein the Flaviviridae viral infection is a HCV infection.

15. A method of inhibiting the RNA-dependent RNA polymerase activity of the enzyme NS5B, encoded by HCV, comprising exposing the enzyme NS5B to an effective amount of the compound according to claim 1 or salts, N-oxides, solvates, hydrates, racemates, enantiomers or diastereomers thereof and optionally another HCV antiviral agent.

16. A method of inhibiting HCV replication comprising exposing a cell infected with HCV to an effective amount of the compound according to claim 1 and optionally another HCV antiviral agent.

17. A pharmaceutical composition comprising the compound according to claim 1 or salts, N-oxides, solvates, hydrates, racemates, enantiomers or diastereomers thereof, a pharmaceutically acceptable carrier and optionally another HCV antiviral agent selected from the group consisting of Ribavarin, an NS5B inhibitor, an NS3/4A protease inhibitor and an NS5A inhibitor.

18. The pharmaceutical composition according to claim 17 additionally comprising at least one immunomodulatory agent.

19. A method for the treatment of a HCV infection which comprises administering an effective amount of the pharmaceutical composition according to claim 17 to a subject in need thereof.

20. A process for producing the compound according to claim 1 comprising the step of coupling a compound of formula (II):

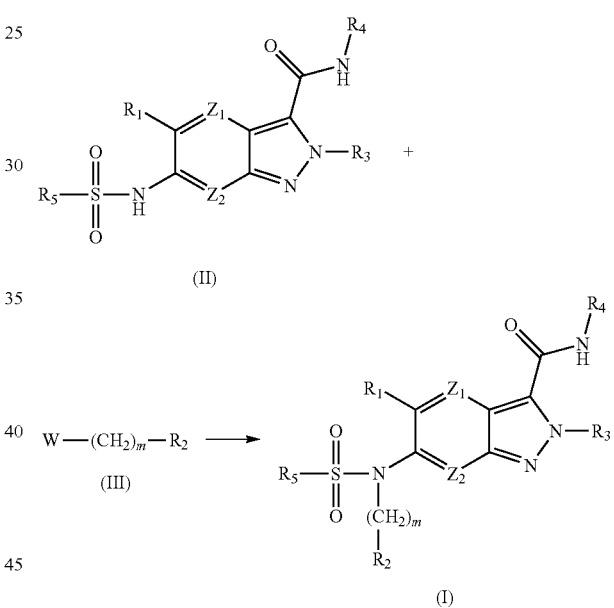

with a compound of general formula (III) under coupling conditions;

wherein

W is hydroxyl, mesylate, tosylate, triflate or halo; and $Z_1$, $Z_2$, $R_1$, $R_2$, $R_3$, $R_4$, $R_5$ and $(CH)_m$ are as defined in claim 1.

21. The HCV polymerase inhibitor according to claim 7 additionally comprising at least one immunomodulatory agent.

22. The pharmaceutical composition according to claim 8 additionally comprising at least one immunomodulatory agent.

23. A method for the treatment of a Flaviviridae viral infection which comprises administering an effective amount of the pharmaceutical composition according to claim 8 to a subject in need thereof.

* * * * *